United States Patent
Lassen et al.

(10) Patent No.: US 9,279,115 B2
(45) Date of Patent: *Mar. 8, 2016

(54) PROTEASES

(75) Inventors: Soren Flensted Lassen, Farum (DK); Carsten Sjoeholm, Allerod (DK); Peter Rahbek Øestergaard, Virum (DK); Morten Fischer, Vedbaek (DK)

(73) Assignee: NOVOZYMES A/S, Bagsvaerd (DK)

(*) Notice: Subject to any disclaimer, the term of this patent is extended or adjusted under 35 U.S.C. 154(b) by 0 days.

This patent is subject to a terminal disclaimer.

(21) Appl. No.: 13/490,566

(22) Filed: Jun. 7, 2012

(65) Prior Publication Data

US 2012/0321747 A1 Dec. 20, 2012

Related U.S. Application Data

(62) Division of application No. 11/570,913, filed as application No. PCT/DK2005/000396 on Jun. 17, 2005, now Pat. No. 8,357,408.

(60) Provisional application No. 60/581,616, filed on Jun. 21, 2004.

(30) Foreign Application Priority Data

Jun. 21, 2004 (DK) .................. 2004 00969

(51) Int. Cl.
*C12N 9/52* (2006.01)
*A23J 3/34* (2006.01)
*A23K 1/165* (2006.01)
*A23K 1/18* (2006.01)
*C11D 3/386* (2006.01)

(52) U.S. Cl.
CPC . *C12N 9/52* (2013.01); *A23J 3/346* (2013.01); *A23K 1/1653* (2013.01); *A23K 1/184* (2013.01); *A23K 1/1826* (2013.01); *A23K 1/1893* (2013.01); *C11D 3/38609* (2013.01); *C11D 3/38618* (2013.01)

(58) Field of Classification Search
CPC .. C12N 9/52; C11D 3/38609; C11D 3/38618; A23K 1/1893; A23K 1/1653; A23K 1/184; A23K 1/1826; A23J 3/346
USPC ......................................... 426/63
See application file for complete search history.

(56) References Cited

U.S. PATENT DOCUMENTS

| | | |
|---|---|---|
| 3,683,069 A | 8/1972 | Hooreman |
| 3,723,250 A | 3/1973 | Aunstrup |
| 3,823,072 A | 7/1974 | Hooreman |
| 3,868,448 A | 2/1975 | Hahn et al. |
| 3,966,971 A | 6/1976 | Morehouse et al. |
| 4,073,884 A | 2/1978 | Hartegen et al. |
| 4,473,644 A * | 9/1984 | Schindler et al. ............ 435/448 |
| 4,518,697 A | 5/1985 | Bartnik |
| 4,927,558 A | 5/1990 | Aaslyng |
| 5,047,240 A | 9/1991 | Hooreman |
| 5,312,748 A | 5/1994 | Liu et al. |
| 5,646,028 A | 7/1997 | Leigh |
| 5,705,379 A | 1/1998 | Wilson et al. |
| 5,811,382 A | 9/1998 | Damhaus |
| 5,877,403 A | 3/1999 | McMaster |
| 6,855,548 B2 | 2/2005 | Sjoeholm et al. |
| 6,960,462 B2 | 11/2005 | Sjoeholm |
| 7,179,630 B2 | 2/2007 | Lassen et al. |
| 7,208,310 B2 | 4/2007 | Lassen et al. |
| 7,485,447 B2 | 2/2009 | Lassen |
| 7,588,926 B2 | 9/2009 | Oestergaard |
| 7,608,444 B2 | 10/2009 | Oestergaard et al. |
| 7,618,801 B2 | 11/2009 | Jones et al. |
| 7,630,836 B2 | 12/2009 | Omura et al. |
| 7,658,965 B2 | 2/2010 | Sjoeholm et al. |
| 7,892,808 B2 | 2/2011 | De Maria et al. |
| 7,906,310 B2 | 3/2011 | Oestergaard et al. |
| 8,067,238 B2 | 11/2011 | Sjoeholm et al. |
| 8,153,396 B2 | 4/2012 | Lynglev et al. |
| 8,357,408 B2 | 1/2013 | Lassen et al. |
| 8,377,677 B2 | 2/2013 | De Maria et al. |
| 8,772,011 B2 | 7/2014 | De Maria et al. |
| 2001/0026797 A1 | 10/2001 | Sjoeholm et al. |
| 2006/0143738 A1 | 6/2006 | Lassen |
| 2006/0147499 A1 | 7/2006 | Oestergaard et al. |

(Continued)

FOREIGN PATENT DOCUMENTS

| | | |
|---|---|---|
| DE | 2004328 | 9/1981 |
| EP | 0 130 756 A1 | 1/1985 |
| EP | 0 300 466 B1 | 1/1989 |
| EP | 0 506 448 A1 | 9/1992 |
| EP | 0 516 200 A1 | 12/1992 |
| EP | 0 647 710 B1 | 4/1995 |
| EP | 0 897 985 A2 | 2/1999 |
| EP | 0 945 502 A1 | 9/1999 |
| JP | 02-255081 | 12/1992 |
| JP | 2003-284571 | 7/2003 |

(Continued)

OTHER PUBLICATIONS

Gayle, R. B. et al. 1993. Identification of regions in interleukin-1alpha important for activity. J. Biol. Chem. 268: 22105-22111.*

(Continued)

*Primary Examiner* — Hamid R Badr

(74) *Attorney, Agent, or Firm* — Elias Lambiris

(57) ABSTRACT

Proteases derived from *Nocardiopsis dassonvillei* subsp. *dassonvillei* DSM 43235, *Nocardiopsis prasina* DSM 15649, *Nocardiopsis prasina* (previously alba) DSM 14010 *Nocardiopsis* sp. DSM 16424, *Nocardiopsis alkaliphila* DSM 44657 and *Nocardiopsis lucentensis* DSM 44048, as well as homologous proteases; their recombinant production in various hosts, including transgenic plants and non-human animals, and their use in animal feed and detergents. The proteases are acid-stable, alkali-stable, and/or thermostable.

7 Claims, No Drawings

(56) References Cited

U.S. PATENT DOCUMENTS

| | | | |
|---|---|---|---|
| 2006/0236414 | A1 | 10/2006 | Lassen |
| 2007/0104764 | A1 | 5/2007 | Jensen et al. |
| 2007/0259404 | A1 | 11/2007 | Jorgensen et al. |
| 2008/0286415 | A1 | 11/2008 | Lassen et al. |
| 2008/0293104 | A1 | 11/2008 | Lassen |
| 2009/0047387 | A1 | 2/2009 | De Maria et al. |
| 2010/0081168 | A1 | 4/2010 | Sjoeholm et al. |
| 2010/0093025 | A1 | 4/2010 | Kalum |
| 2010/0093633 | A1 | 4/2010 | De Maria et al. |
| 2010/0255153 | A1 | 10/2010 | Oestergaard et al. |
| 2010/0322915 | A1 | 12/2010 | Svendsen et al. |
| 2011/0081450 | A1 | 4/2011 | Lynglev et al. |
| 2011/0097448 | A1 | 4/2011 | Wong et al. |
| 2011/0097760 | A1 | 4/2011 | Lynglev et al. |
| 2012/0321746 | A1 | 12/2012 | Lassen et al. |
| 2012/0321747 | A1 | 12/2012 | Lassen et al. |

FOREIGN PATENT DOCUMENTS

| | | | |
|---|---|---|---|
| JP | 2004-043660 | | 2/2004 |
| WO | 88/03947 | A1 | 6/1988 |
| WO | 91/00345 | A1 | 1/1991 |
| WO | 91/10723 | A1 | 7/1991 |
| WO | 92/19729 | A1 | 11/1992 |
| WO | 95/02044 | A1 | 1/1995 |
| WO | 95/21540 | A1 | 8/1995 |
| WO | 95/28850 | A1 | 11/1995 |
| WO | 96/05739 | A1 | 2/1996 |
| WO | 98/56260 | A2 | 12/1998 |
| WO | 99/53038 | A2 | 10/1999 |
| WO | 01/58276 | A2 | 8/2001 |
| WO | 2004/070106 | A2 | 8/2004 |
| WO | 2004/072221 | A1 | 8/2004 |
| WO | 2004/072279 | A2 | 8/2004 |
| WO | 2004/111219 | A1 | 12/2004 |
| WO | 2004/111220 | A1 | 12/2004 |
| WO | 2004/111221 | A1 | 12/2004 |
| WO | 2004/111222 | A1 | 12/2004 |
| WO | 2004/111223 | A1 | 12/2004 |
| WO | 2004/111224 | A1 | 12/2004 |
| WO | 2005/115445 | A1 | 12/2005 |

OTHER PUBLICATIONS

Whisstock, J. C. et al. 2003. Prediction of protein function from protein sequence and structure. Quarterly Rev. Biophys. 36: 307-340.*
Witkowski, A. et al. 1999. Conversion of a beta-ketoacyl synthase to a malonyl decarboxylase. Biochemistry. 38: 11643-11650.*
Seffernick, J. L. et al. 2001. Melanine deaminase and atrozine chlorohdrolase; 98 precent identical but functionally different. J. Bacteriol. 183: 2405-2410.*
Score-proteins-Search-SEQ-ID-NO-2.*
NCBI-database-ADH66923.*
Guo et al. proc. Nat. Acad. Sci. 101(25): 9205-9210 (2004).*
Altshul et al., GenPept Accession No. PQ0104 (1997).
Barrett et al., Handbook of Proteolytic Enzymes pp. 2-3 (1998).
Caine et al., Animal Feed Science Technology, vol. 71, pp. 177-183 (1998).
Dixit et al., Biochimica et Biophysica Acta, vol. 1523, No. 2-3, pp. 261-268 (2000).
FASTA Sequence alignment (1993).
Fernandez-Abalos et al., Microbiology, vol. 149, pp. 1623-1632 (2003).
Gayle et al., Journal of Biological Chemistry, vol. 268, No. 29, pp. 22105-22111 (1993).
Gill et al., Analytical Biochemistry, vol. 182, pp. 319-326 (1989).
Goodenough et al., Molecular Biotechnology, vol. 4, No. 1, pp. 151-166 (1995).
Henderson et al., Journal of Bacteriology, vol. 169, No. 8, pp. 3778-3784 (1987).
Heringa et al., Protein Engineering, vol. 8, No. 1, pp. 21-30 (1995).
Higgins et al., Gene, vol. 73, pp. 237-244 (1988).
Kaneda et al., Journal of Biochemistry, vol. 78, pp. 1287-1296 (1975).
Kim et al., Korean Biotechnology Journal, vol. 26, No. 1, pp. 81-85 (1993).
Lao et al., Applied and Environmental Microbiology, vol. 62, No. 11, pp. 4256-4259 (1996).
Merops Database, Alignment of Subfamily S1E Peptidases (2004).
Michalik et al., Ukr Biokhim Zh, vol. 69. No. 3, pp. 28-35 (1997).
Mitsuiki et al., Bioscience Biotechnology Biochemistry, vol. 66, No. 1, pp. 164-167 (2002).
Mitsuiki et al., Database EMBL, Accession No. AY151208 (2004).
Mitsuiki et al., Enzyme and Microbial Technology, vol. 34, No. 5, pp. 482-489 (2004).
Moreira et al., World Journal of Microbiol Biotechnology, vol. 18, No. 4, pp. 307-312 (2002).
Needleman et al., Journal of Molecular Biology, vol. 48, pp. 443-453 (1970).
Ofagian, Enzyme and Microbial Technology, vol. 33, No. 2-3, pp. 137-149 (2003).
Refstie et al., Aquaculture, vol. 162, pp. 301-312 (1998).
Sambrook et al., Molecular Cloning 3rd Edition vol. 2, pp. 10.47-10.48 (2001).
Screen et al., Journal of Biological Chemistry, vol. 275, No. 9, pp. 6689-6694 (2000).
Sidhu et al., Journal of Biological Chemistry, vol. 269, No. 31, pp. 20167-20171 (1994).
Smith et al., Analytical Biochemistry, vol. 150, pp. 76-85 (1985).
Tsujibo et al., Agricultural and Biological Chemistry, vol. 54, No. 8, pp. 2177-2179 (1990).
Tsujibo et al., Journal of Applied Bacteriology, vol. 69, pp. 520-529 (1990).
Tsujibo et al., Applied and Environmental Microbiology, vol. 69, No. 2, pp. 894-900 (2003).
Vieille et al., Microbiology and Molecular Biology Reviews, vol. 65, No. 1, pp. 1-43 (2001).
Whisstock et al., Quarterly Reviews of Biophysics, vol. 36, No. 3, pp. 307-340 (2003).
DK PA 1996 00013—Database A_Geneseq, Accession No. AAW92997 (1999).
DK PA 1996 00013—Database N_Geneseq, Accession No. AAX22316 (1999).
EP 0 506 448 A1—Database GeneSeq Nucleotide, Accession No. AAQ29011—Seq_0001 (1992).
EP 0 506 448 A1—Database GeneSeq Nucleotide, Accession No. AAQ29011—Seq_0011 (1992).
JP 2003-284571—Database GeneseqN, Accession No. ADF43563 (2003).
JP 2003-284571—Database GeneseqP, Accession No. ADF43564 (2003).
Sequence Alignment of Protein disclosed in WO 2001/58276, Accession No. AAU07125 (2003).
Database EMBL, Accession No. AY151208, Nocardiopsis sp. TOA-1 serine protease (napA) gene complete cds, XP-002308395 (May 16, 2004).
WO 2004/070106 A1—Derwent Accession No. 2004-625510 (2004).
Yum et al., GenBank Accession No. X74103 (1993).

* cited by examiner

PROTEASES

CROSS-REFERENCE TO RELATED APPLICATIONS

This application is a divisional of U.S. application Ser. No. 11/570,913 filed on Dec. 19, 2006, now U.S. Pat. No. 8,357,408, which is a 35 U.S.C. 371 national application of PCT/DK2005/000396 filed on Jun. 17, 2005, which claims priority or the benefit under 35 U.S.C. 119 of Danish application no. PA 2004 00969 filed Jun. 21, 2004 and U.S. provisional application No. 60/581,616 filed Jun. 21, 2004, the contents of which are fully incorporated herein by reference.

FIELD OF THE INVENTION

The present invention relates to isolated polypeptides having protease activity and isolated nucleic acid sequences encoding the polypeptides. The invention also relates to nucleic acid constructs, vectors, and host cells, including plant and animal cells, comprising the nucleic acid sequences, as well as methods for producing and using the polypeptides, in particular the use of the polypeptides in animal feed, and detergents.

BACKGROUND OF THE INVENTION

Proteases derived from *Nocardiopsis* sp. NRRL 18262 and *Nocardiopsis dassonvillei* NRRL 18133 are disclosed in WO 88/03947. The DNA and amino acid sequences of the protease derived from *Nocardiopsis* sp. NRRL 18262 are shown in DK application no. 1996 00013. WO 01/58276 discloses the use in animal feed of acid-stable proteases related to the protease derived from *Nocardiopsis* sp. NRRL 18262, as well as a protease derived from *Nocardiopsis alba* DSM 14010.

JP 2-255081-A discloses a protease derived from *Nocardiopsis* sp. strain OPC-210 (FERM P-10508), however without sequence information. The strain is no longer available, as the deposit was withdrawn.

DD 2004328 discloses a proteolytic preparation derived from *Nocardiopsis dassonvillei* strain ZIMET 43647, however without sequence information. The strain appears to be no longer available.

JP 2003284571-A discloses the amino acid sequence and the corresponding DNA sequence of a protease derived from *Nocardiopsis* sp. TOA-1 (FERM P-18676). The sequence has been entered in GENESEQP with no. ADF43564.

It is an object of the present invention to provide alternative proteases, in particular for use in animal feed and/or detergents.

SUMMARY OF THE INVENTION

A number of proteases were cloned, purified and characterized. These proteases are designated as follows: Protease L1a derived from *Nocardiopsis dassonvillei* subsp. *dassonvillei* DSM 43235 (see SEQ ID NOs. 1 and 2); protease L1b derived from *Nocardiopsis prasina* DSM 15649 (see SEQ ID NOs: 3 and 4); protease L1c derived from *Nocardiopsis prasina* (previously alba) DSM 14010 (see SEQ ID NOs: 5 and 6); protease L2a derived from *Nocardiopsis* sp. DSM 16424 (see SEQ ID NOs: 7 and 8); protease L2b derived from *Nocardiopsis alkaliphila* DSM 44657 (see SEQ ID NOs: 9 and 10); and protease L2c derived from *Nocardiopsis lucentensis* DSM 44048 (see SEQ ID NOs: 11 and 12).

In a first aspect, the invention relates to an isolated polypeptide having protease activity, selected from the group consisting of: (a) a polypeptide having an amino acid sequence which has a degree of identity to amino acids 1-192 of SEQ ID NO: 6 of at least 71.5%; (b) a polypeptide which is encoded by a nucleic acid sequence which hybridizes under very high stringency conditions with (i) nucleotides 574-1149 of SEQ ID NO:5, (ii) a subsequence of (i) of at least 100 nucleotides, and/or (iii) a complementary strand of (i), or (ii); (c) a variant of the polypeptide having an amino acid sequence of amino acids 1-192 of SEQ ID NO: 6 comprising a substitution, deletion, extension, and/or insertion of one or more amino acids; (d) an allelic variant of (a), or (b); and (e) a fragment of (a), (b), or (d) that has protease activity.

In five alternative aspects, corresponding to the five sets of particular embodiments set forth at the end of the present description, the present invention also relates to:

An isolated polypeptide having protease activity, selected from the group consisting of: (a) a polypeptide having an amino acid sequence which has a degree of identity to amino acids 1-192 of SEQ ID NO: 4 of at least 69.9%; (b) a polypeptide which is encoded by a nucleic acid sequence which hybridizes under low stringency conditions with (i) nucleotides 574-1149 of SEQ ID NO:3, (ii) a subsequence of (i) of at least 100 nucleotides, and/or (iii) a complementary strand of (i), or (ii); (c) a variant of the polypeptide having an amino acid sequence of amino acids 1-192 of SEQ ID NO: 4 comprising a substitution, deletion, extension, and/or insertion of one or more amino acids; (d) an allelic variant of (a), or (b); and (e) a fragment of (a), (b), or (d) that has protease activity.

An isolated polypeptide having protease activity, selected from the group consisting of: (a) a polypeptide having an amino acid sequence which has a degree of identity to amino acids 1-192 of SEQ ID NO: 2 of at least 75.1%; (b) a polypeptide which is encoded by a nucleic acid sequence which hybridizes under low stringency conditions with (i) nucleotides 568-1143 of SEQ ID NO: 1, (ii) a subsequence of (i) of at least 100 nucleotides, and/or (iii) a complementary strand of (i), or (ii); (c) a variant of the polypeptide having an amino acid sequence of amino acids 1-192 of SEQ ID NO: 2 comprising a substitution, deletion, extension, and/or insertion of one or more amino acids; (d) an allelic variant of (a), or (b); and (e) a fragment of (a), (b), or (d) that has protease activity.

An isolated polypeptide having protease activity, selected from the group consisting of: (a) a polypeptide having an amino acid sequence which has a degree of identity to amino acids 1-189 of SEQ ID NO: 8 of at least 92.2%; (b) a polypeptide which is encoded by a nucleic acid sequence which hybridizes under low stringency conditions with (i) nucleotides 586-1152 of SEQ ID NO: 7, (ii) a subsequence of (i) of at least 100 nucleotides, and/or (iii) a complementary strand of (i), or (ii); (c) a variant of the polypeptide having an amino acid sequence of amino acids 1-189 of SEQ ID NO: 8 comprising a substitution, deletion, extension, and/or insertion of one or more amino acids; (d) an allelic variant of (a), or (b); and (e) a fragment of (a), (b), or (d) that has protease activity.

An isolated polypeptide having protease activity, selected from the group consisting of: (a) a polypeptide having an amino acid sequence which has a degree of identity to amino acids 1-189 of SEQ ID NO: 10 of at least 93.2%; (b) a polypeptide which is encoded by a nucleic acid sequence which hybridizes under low stringency conditions with (i) nucleotides 586-1149 of SEQ ID NO: 9, (ii) a subsequence of (i) of at least 100 nucleotides, and/or (iii) a complementary strand of (i), or (ii); (c) a variant of the polypeptide having an amino acid sequence of amino acids 1-189 of SEQ ID NO: 10 comprising a substitution, deletion, extension, and/or insertion of one or more amino acids; (d) an allelic variant of (a), or (b); and (e) a fragment of (a), (b), or (d) that has protease activity.

An isolated polypeptide having protease activity, selected from the group consisting of: (a) a polypeptide having an amino acid sequence which has a degree of identity to amino acids 1-189 of SEQ ID NO: 12 of at least 83.3%; (b) a polypeptide which is encoded by a nucleic acid sequence which hybridizes under low stringency conditions with (i) nucleotides 586-1152 of SEQ ID NO: 11, (ii) a subsequence of (i) of at least 100 nucleotides, and/or (iii) a complementary strand of (i), or (ii); (c) a variant of the polypeptide having an amino acid sequence of amino acids 1-189 of SEQ ID NO: 12 comprising a substitution, deletion, extension, and/or insertion of one or more amino acids; (d) an allelic variant of (a), or (b); and (e) a fragment of (a), (b), or (d) that has protease activity.

The invention also relates to isolated nucleic acid sequences encoding the above polypeptides and to nucleic acid constructs, vectors, and host cells comprising the nucleic acid sequences as well as methods for producing and using the polypeptides, in particular within animal feed, and detergents.

DETAILED DESCRIPTION OF THE INVENTION

Polypeptides Having Protease Activity

Polypeptides having protease activity, or proteases, are sometimes also designated peptidases, proteinases, peptide hydrolases, or proteolytic enzymes. Proteases may be of the exo-type that hydrolyses peptides starting at either end thereof, or of the endo-type that act internally in polypeptide chains (endopeptidases). Endopeptidases show activity on N- and C-terminally blocked peptide substrates that are relevant for the specificity of the protease in question.

The term "protease" is defined herein as an enzyme that hydrolyzes peptide bonds. It includes any enzyme belonging to the EC 3.4 enzyme group (including each of the thirteen subclasses thereof). The EC number refers to Enzyme Nomenclature 1992 from NC-IUBMB, Academic Press, San Diego, Calif., including supplements 1-5 published in *Eur. J. Biochem.* 223: 1-5 (1994); *Eur. J. Biochem.* 232: 1-6 (1995); *Eur. J. Biochem.* 237: 1-5 (1996); *Eur. J. Biochem.* 250: 1-6 (1997); and *Eur. J. Biochem.* 264: 610-650 (1999); respectively. The nomenclature is regularly supplemented and updated; see, e.g., the World Wide Web (WWW) at chem.qmw.ac.uk/iubmb/enzyme/index.html.

Proteases are classified on the basis of their catalytic mechanism into the following groups: Serine proteases (S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

In particular embodiments, the proteases of the invention and for use according to the invention are selected from the group consisting of:

(a) proteases belonging to the EC 3.4.-.-enzyme group;
(b) Serine proteases belonging to the S group of the above Handbook;
(c) Serine proteases of peptidase family S2A; and/or
(d) Serine proteases of peptidase family S1E as described in *Biochem. J.* 290:205-218 (1993) and in MEROPS protease database, release 6.20, Mar. 24, 2003, (www.merops.ac.uk). The database is described in Rawlings et al., 2002, MEROPS: the protease database. *Nucleic Acids Res.* 30: 343-346.

For determining whether a given protease is a Serine protease, and a family S2A pro-tease, reference is made to the above Handbook and the principles indicated therein. Such determination can be carried out for all types of proteases, be it naturally occurring or wild-type proteases; or genetically engineered or synthetic proteases.

Protease activity can be measured using any assay, in which a substrate is employed, that includes peptide bonds relevant for the specificity of the protease in question. Assay-pH and assay-temperature are likewise to be adapted to the protease in question. Examples of assay-pH-values are pH 2, 3, 4, 5, 6, 7, 8, 9, 10, 11, or 12. Examples of assay-temperatures are 30, 35, 37, 40, 45, 50, 55, 60, 65, 70, 80, 90, or 95° C.

Examples of protease substrates are casein, such as Azurine-Crosslinked Casein (AZCL-casein). Three protease assays are described in Examples 4-5 herein, either of which can be used to determine protease activity. For the purposes of this invention, the so-called pNA Assay is a preferred assay.

There are no limitations on the origin of the protease of the invention and/or for use according to the invention. Thus, the term protease includes not only natural or wild-type proteases obtained from microorganisms of any genus, but also any mutants, variants, fragments etc. thereof exhibiting protease activity, as well as synthetic proteases, such as shuffled proteases, and consensus proteases. Such genetically engineered proteases can be prepared as is generally known in the art, e.g., by Site-directed Mutagenesis, by PCR (using a PCR fragment containing the desired mutation as one of the primers in the PCR reactions), or by Random Mutagenesis. The preparation of consensus proteins is described in, e.g., EP 897985. Gene shuffling is generally described in, e.g., WO 95/22625 and WO 96/00343. Recombination of protease genes can be made independently of the specific sequence of the parents by synthetic shuffling as described in Ness et al., 2002, *Nature Biotechnology* 20(12): 1251-1255. Synthetic oligonucleotides degenerated in their DNA sequence to provide the possibility of all amino acids found in the set of parent proteases are designed and the genes assembled according to the reference. The shuffling can be carried out for the full length sequence or for only part of the sequence and then later combined with the rest of the gene to give a full length sequence. The proteases of SEQ ID NOs: 2, 4, 6, 8, 10, and 12, as well as the *Nocardiopsis* proteases described in the prior documents listed above, are particular examples of such parent proteases which can be subjected to shuffling as described above, to provide additional proteases of the invention. The term "obtained from" as used herein in connection with a given source shall mean that the polypeptide encoded by the nucleic acid sequence is produced by the source or by a cell in which the nucleic acid sequence from the source is present. In a preferred embodiment, the polypeptide is secreted extracellularly.

In a specific embodiment, the protease is a low-allergenic variant, designed to invoke a reduced immunological response when exposed to animals, including man. The term immunological response is to be understood as any reaction by the immune system of an animal exposed to the protease. One type of immunological response is an allergic response leading to increased levels of IgE in the exposed animal. Low-allergenic variants may be prepared using techniques known in the art. For example the protease may be conjugated with polymer moieties shielding portions or epitopes of the protease involved in an immunological response. Conjugation with polymers may involve in vitro chemical coupling of polymer to the protease, e.g., as described in WO 96/17929, WO 98/30682, WO 98/35026, and/or WO 99/00489. Conjugation may in addition or alternatively thereto involve in vivo coupling of polymers to the protease. Such conjugation may be achieved by genetic engineering of the nucleotide sequence encoding the protease, inserting consensus sequences encoding additional glycosylation sites in the protease and expressing the protease in a host capable of glycosylating the protease, see, e.g., WO 00/26354. Another way of providing low-allergenic variants is genetic engineering of the nucleotide sequence encoding the protease so as to cause the proteases to self-oligomerize, effecting that protease monomers may shield the epitopes of other protease monomers and thereby lowering the antigenicity of the oligomers. Such products and their preparation is described, e.g., in WO 96/16177. Epitopes involved in an immunological response may be identified by various methods such as the phage display method described in WO 00/26230 and WO 01/83559, or the random approach described in EP 561907. Once an epitope has been identified, its amino acid sequence may be altered to produce altered immunological properties of the protease by known gene manipulation techniques such as site directed mutagenesis (see, e.g., WO 00/26230, WO 00/26354 and/or WO 00/22103) and/or conjugation of a polymer may be done in sufficient proximity to the epitope for the polymer to shield the epitope.

The various aspects of the present invention relate to isolated polypeptides having protease activity (for short "proteases"), as well as the corresponding isolated nucleic acid sequences, said polypeptides, or nucleic acids, respectively, comprising an amino acid sequence, or a nucleic acid sequence, respectively, having a certain degree of identity to a specified fragment of an amino acid sequence, or a nucleic acid sequence, respectively, with a specified SEQ ID NO. The fragments specified correspond to the mature polypeptides, or the mature polypeptide encoding parts of the nucleic acid sequences, respectively.

For purposes of the present invention the degree of identity between two amino acid sequences, as well as the degree of identity between two nucleotide sequences, is determined by the program "align" which is a Needleman-Wunsch alignment (i.e., a global alignment). The program is used for alignment of polypeptide, as well as nucleotide sequences. The default scoring matrix BLOSUM50 is used for polypeptide alignments, and the default identity matrix is used for nucleotide alignments. The penalty for the first residue of a gap is –12 for polypeptides and –16 for nucleotides. The penalties for further residues of a gap are –2 for polypeptides, and –4 for nucleotides.

"Align" is part of the FASTA package version v20u6 (see Pearson and Lipman, 1988, "Improved Tools for Biological Sequence Analysis", *PNAS* 85:2444-2448, and Pearson, 1990, "Rapid and Sensitive Sequence Comparison with FASTP and FASTA," *Methods in Enzymology* 183: 63-98). FASTA protein alignments use the Smith-Waterman algorithm with no limitation on gap size (see "Smith-Waterman algorithm", Smith and Waterman, 1981, *J. Mol. Biol.* 147: 195-197).

In particular embodiments, the polypeptide of the invention has a degree of identity to the mature parts of either of SEQ ID NO: 2, 4, 6, 8, 10, or 12 of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99%.

In other particular embodiments, the nucleic acid sequence of the invention has a degree of identity to the mature peptide encoding part of either of SEQ ID NO: 1, 3, 5, 7, 9, or 11 of at least 78%, 79%, 80%, 81%, 82%, 83%, 84%, 85%, 86%, 87%, 88%, 89%, 90%, 91%, 92%, 93%, 94%, 95%, 96%, 97%, 98%, or at least 99%.

In still further particular embodiments, the protease of the invention has an amino acid sequence that differs by (i) no more than twenty, nineteen, eighteen, seventeen, sixteen, fifteen, fourteen, thirteen, twelve, or no more than eleven amino acids; (ii) no more than ten, nine, eight, seven, six, five, four, three, two, or no more than one amino acid; (iii) ten, or by nine, or by eight, or by seven, or by six, or by five amino acids; or (iv) four, or by three, or by two amino acids, or by one amino acid from the mature parts of either of SEQ ID NO: 2, 4, 6, 8, 10, and 12.

In a still further particular embodiment, the protease of the invention comprises the amino acid sequence of the mature parts of either of SEQ ID NO: 2, 4, 6, 8, 10, or 12; or is an allelic variant thereof; or a fragment thereof that has protease activity.

In a further preferred embodiment, the polypeptides of the present invention consist of the mature peptide part of either of SEQ ID NO: 2, 4, 6, 8, 10, or 12; or allelic variants thereof; or fragments thereof that have protease activity.

A fragment of either of SEQ ID NO: 2, 4, 6, 8, 10, or 12 is a polypeptide having one or more amino acids deleted from the amino and/or carboxyl terminus of these amino acid sequences. In one embodiment a fragment contains at least 75 amino acid residues, or at least 100 amino acid residues, or at least 125 amino acid residues, or at least 150 amino acid residues, or at least 160 amino acid residues, or at least 165 amino acid residues, or at least 170 amino acid residues, or at least 175 amino acid residues.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The present invention also relates to isolated polypeptides having protease activity and which are encoded by nucleic acid sequences which hybridize under very low, or low, or medium, or medium-high, or high, or very high stringency conditions with a nucleic acid probe which hybridizes under the same conditions with (a) either of SEQ ID NO: 1, 3, 5, 7, 9, or 11, or the mature peptide encoding parts thereof; (b) a subsequence of (a), or (c) a complementary strand of (a), or (b) (Sambrook et al., 1989, Molecular Cloning, A Laboratory Manual, 2nd edition, Cold Spring Harbor, N.Y.). In particular embodiments the nucleic acid probe is selected from amongst the nucleic acid sequences of (a), (b), or (c) above.

The subsequence of (a) may be at least 100 nucleotides, or in another embodiment at least 200 nucleotides. Moreover, the subsequence may encode a polypeptide fragment that has protease activity.

The nucleic acid sequences of either of SEQ ID NO: 1, 3, 5, 7, 9, or 11, or the mature peptide encoding parts thereof, or a subsequence thereof, as well as the amino acid sequences of either of SEQ ID NO: 2, 4, 6, 8, 10, or 12, or a fragment thereof, may be used to design a nucleic acid probe to identify and clone DNA encoding polypeptides having protease activity from strains of the same or different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

Thus, a genomic DNA or cDNA library prepared from such other organisms may be screened for DNA that hybridizes with the probes described above and which encodes a polypeptide having protease activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with either of SEQ ID NO: 1, 3, 5, 7, 9, or 11, or a subsequence thereof, the carrier material is used in a Southern blot. For purposes of the present invention, hybridization indicates that the nucleic acid sequence hybridizes to a labeled nucleic acid probe corresponding to the nucleic acid sequence shown in either of these SEQ ID NOs, its complementary strand, or a subsequence thereof, under very low to very high stringency conditions. Molecules to which the nucleic acid probe hybridizes under these conditions are detected using X-ray film.

In a particular embodiment, the nucleic acid probe is a nucleic acid sequence which encodes the mature peptide parts of either of SEQ ID NO: 2, 4, 6, 8, 10, or 12, or subsequences thereof. In another embodiment, the nucleic acid probe is those nucleotides of either of SEQ ID NO: 1, 3, 5, 7, 9, or 11 that correspond to the mature polypeptide coding regions.

For long probes of at least 100 nucleotides in length, very low to very high stringency conditions are defined as prehybridization and hybridization at 42° C. in 5×SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency). Preferably, the wash is conducted using either 0.2×SSC, 0.1×SSC or 0.02×SSC, the other wash conditions being unamended (i.e., wash three times, each for 15 minutes; include 0.2% SDS, washing preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency)).

For short probes about 15 nucleotides to about 70 nucleotides in length, stringency conditions are defined as prehybridization, hybridization, and washing post-hybridization at 5° C. to 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes about 15 nucleotides to about 70 nucleotides in length, the carrier material is washed once in 6×SSC plus 0.1% SDS for 15 minutes and twice each for 15 minutes using 6×SSC at 5° C. to 10° C. below the calculated $T_m$.

The present invention also relates to variants of the polypeptides comprising the mature parts of either of the amino acid sequences SEQ ID NO: 2, 4, 6, 8, 10, or 12, and comprising a substitution, deletion, and/or insertion of one or more amino acids.

The amino acid sequences of the variant polypeptides may differ from the amino acid sequence of the mature parts of either of SEQ ID NO: 2, 4, 6, 8, 10, or 12, by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Accordingly, for example, the invention relates to a polypeptide having, or comprising, a sequence as set forth in either of SEQ ID NO: 2, 4, 6, 8, 10, or 12, wherein conservative amino acid substitutions comprise replacements, one for another, among the basic amino acids (arginine, lysine and histidine), among the acidic amino acids (glutamic acid and aspartic acid), among the polar amino acids (glutamine and asparagine), among the hydrophobic amino acids (alanine, leucine, isoleucine and valine), among the aromatic amino acids (phenylalanine, tryptophan and tyrosine), and among the small amino acids (glycine, alanine, serine, threonine and methionine), or any combination thereof, or active fragments thereof. Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

A polypeptide of the present invention may be a bacterial or fungal polypeptide. The fungal polypeptide may be derived from a filamentous fungus or from a yeast.

In particular embodiments, the polypeptide of the invention is i) a bacterial protease; ii) a protease of the phylum Actinobacteria; iii) of the class Actinobacteria; iv) of the order Actinomycetales v) of the family Nocardiopsaceae; vi) of the genus *Nocardiopsis*; and/or a protease derived from vii) *Nocardiopsis* species such as *Nocardiopsis alba, Nocardiopsis alkaliphila, Nocardiopsis antarctica, Nocardiopsis prasina, Nocardiopsis composta, Nocardiopsis exhalans, Nocardiopsis halophila, Nocardiopsis halotolerans, Nocardiopsis kunsanensis, Nocardiopsis listed, Nocardiopsis lucentensis, Nocardiopsis metallicus, Nocardiopsis synnemataformans,*

*Nocardiopsis trehalosi, Nocardiopsis tropica, Nocardiopsis umidischolae, Nocardiopsis xinjiangensis*, or *Nocardiopsis dassonvillei*, for example from either of *Nocardiopsis dassonvillei* subsp. *dassonvillei* DSM 43235, *Nocardiopsis prasina* DSM 15649, *Nocardiopsis prasina* (previously alba) DSM 14010, *Nocardiopsis* sp. DSM 16424, *Nocardiopsis alkaliphila* DSM 44657, or from *Nocardiopsis lucentensis* DSM 44048.

In a particular embodiment, the protease derives from *Nocardiopsis alba, Nocardiopsis alkaliphila, Nocardiopsis dassonvillei, Nocardiopsis lucentensis, Nocardiopsis prasina*, or *Nocardiopsis* sp.

The above taxonomy is according to the chapter: The road map to the Manual by G. M. Garrity & J. G. Holt in Bergey's Manual of Systematic Bacteriology, 2001, second edition, volume 1, David R. Bone, Richard W. Castenholz.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

As defined herein, an "isolated" polypeptide is a polypeptide which is essentially free of other non-protease polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Polypeptides encoded by nucleic acid sequences of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

In a particular embodiment, the polypeptides of the invention are acid-stable. For the present purposes, the term acid-stable means that the residual activity after 2 hours of incubation at pH 2.0, pH 2.5 or pH 3.0 and 37° C., is at least 50%, as compared to the residual activity of a corresponding sample incubated for 2 hours at pH 9.0 and 5° C. In a particular embodiment, the residual activity is at least 55%, 60%, 65%, 70%, 75%, 80%, 85%, or at least 90%. A suitable assay for determining acid-stability is the pH-stability assay of Example 2.

In another particular embodiment, the polypeptides of the invention are alkali-stable. For the present purposes, the term alkali-stable means that the residual activity after 2 hours of incubation at pH 12.0 and 37° C., is at least 85%, as compared to the residual activity of a corresponding sample incubated for 2 hours at pH 9.0 and 5° C. In a particular embodiment, the residual activity is at least 86%, 87%, 88%, 89%, 90%, 91%, or at least 92%. A suitable assay for determining alkali-stability is the pH-stability assay of Example 4.

In still further particular embodiments, the polypeptides of the invention and for use according to the invention have i) a relative activity at 15° C. and pH 9 of at least 0.02, 0.04, 0.06, 0.08, 0.10, or at least 0.11; ii) a relative activity at 25° C. and pH 9 of at least 0.05, 0.10, 0.15, or at least 0.17; and/or iii) a relative activity at 37° C. and pH 9 of at least 0.05, 0.10, 0.15, 0.20, 0.25, or at least 0.30. The temperature-profile test of Example 4 is used for these determinations.

In still further particular embodiments, the polypeptides of the invention have a Tm, as determined by DSC, of at least 76.6° C., or of at least 77, 78, or at least 78.2° C. Tm is determined at pH 7.0 as described in Example 7.

In an additional particular embodiment the protease of the invention exhibits a specific activity on haemoglobin at pH 7.5 and 25° C. of at least 38.4 AU/g. The specific activity may be determined as described in Example 5. The protease of the invention may exhibit a specific activity of at least 39, 40, 41, 42, 43, 44, 45, 46, 47, 48, 49, 49.8, or at least 50 AU/g. In a further particular embodiment, the protease of the invention is capable of improving, by at least 13% as compared to the blank, the level of digestible protein of a maize/soybean meal diet (SBM:Maize=2:3 (w/w)) in a monogastric in vitro digestion model. The model includes a gastric digestion step (1.0 hour at pH 3.0 and 40° C.), and a subsequent intestinal digestion step (4.5 hours at pH 6.8 and 40° C.). The model also includes addition of pepsin (3000 U/g, in the gastric digestion step), and of pancreatin (8 mg/g, in the intestinal digestion step). The protease dosage is 100 mg protease enzyme protein (EP) per kg of diet. A suitable model is described in Example 8. The level of improvement may be at least 14%, 15%, or at least 16%.

In still further particular embodiments, the invention excludes the protease derived from (i) *Nocardiopsis dassonvillei* NRRL 18133 which is disclosed in WO 88/03947; (ii) *Nocardiopsis* sp. strain OPC-210 (FERM P-10508) which is disclosed in JP 2-255081-A; and/or (iii) the protease derived from strain ZIMET 43647 of the species *Nocardiopsis dassonvillei* which is disclosed in DD 2004328.

Nucleic Acid Sequences

The present invention also relates to isolated nucleic acid sequences that encode a polypeptide of the present invention. Particular nucleic acid sequences of the invention are (i) nucleotides 1-1143, 1-87, 88-567, and 568-1143 of SEQ ID NO: 1; (ii) nucleotides 1-1149, 1-87, 88-573, and 574-1149 of SEQ ID NO: 3; (iii) nucleotides 1-1149, 1-87, 88-573, and 574-1149 of SEQ ID NO: 5; (iv) nucleotides 1-1152, 1-87, 88-585, and 586-1152 of SEQ ID NO: 7; (v) nucleotides 1-1149, 1-87, 88-585, and 586-1149 of SEQ ID NO: 9; and (vi) nucleotides 1-1152, 1-87, 88-585, and 586-1152 of SEQ ID NO: 11; and (vii) any combination thereof.

Particularly preferred nucleotides are (i) nucleotides 568-1143 of SEQ ID NO: 1; (ii) nucleotides 574-1149 of SEQ ID NO: 3; (iii) nucleotides 574-1149 of SEQ ID NO: 5; (iv) nucleotides 586-1152 of SEQ ID NO: 7; (v) nucleotides 586-

1149 of SEQ ID NO: 9; and (vi) nucleotides 586-1152 of SEQ ID NO: 11; corresponding to the mature polypeptide encoding parts or regions.

The present invention also encompasses nucleic acid sequences which encode a polypeptide having the mature parts of either of SEQ ID NO: 2, 4, 6, 8, 10 or 12, which differ from the corresponding parts of SEQ ID NO: 1, 3, 5, 7, 9, or 11, respectively, by virtue of the degeneracy of the genetic code. The present invention also relates to subsequences of either of SEQ ID NO: 1, 3, 5, 7, 9, or 11 which encode fragments of SEQ ID NO: 2, 4, 6, 8, 10 or 12, respectively, and which have protease activity.

A subsequence of either of SEQ ID NO: 1, 3, 5, 7, 9, or 11 is a nucleic acid sequence encompassed by SEQ ID NO: 1, 3, 5, 7, 9 or 11, except that one or more nucleotides from the 5' and/or 3' end have been deleted. Preferably, a subsequence contains at least 100, 125, 150, 175, 200, or at least 225 nucleotides, more preferably at least 300 nucleotides, even more preferably at least 325, 350, 375, 400, 425, 450, 475, 500, 525, 550, or at least 560 nucleotides.

The present invention also relates to nucleotide sequences which have a degree of identity to the mature peptide encoding parts of either of SEQ ID NO: 1, 3, 5, 7, 9, or 11 of at least 77.7%, preferably of at least 78%, 79%, 80%, 81%, 82%, 83%, 84%, 85%, 86%, 87%, 88%, 89%, 90%, 91%, 92%, 93%, 94%, 95%, 96%, 97%, 98%, or at least 99%.

For determining the degree of nucleotide identity, the program "align" is used which is referred to above.

The present invention also relates to mutant nucleic acid sequences comprising at least one mutation in any of the nucleotides of (i)-(vi) listed above, preferably the mature peptide encoding parts thereof, in which the mutant nucleic acid sequence encodes a polypeptide which (i) consists of the amino acid sequences of either of SEQ ID NO: 2, 4, 6, 8, 10, or 12, preferably the mature peptide parts thereof, or (ii) is a variant of any of the sequences of (i), wherein the variant comprises a substitution, deletion, and/or insertion of one or more amino acids, or (iii) is an allelic variant of any of the sequences of (i), or (iv) is a fragment of any of the sequences of (i).

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of *Nocardiopsis*, or another or related organism and thus, for example, may be an allelic or species variant of the polypeptide encoding region of the nucleic acid sequence.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, allergenicity, or the like. The variant sequence may be constructed on the basis of the nucleic acid sequence presented as the polypeptide encoding part, or mature peptide encoding part, of either of SEQ ID NO: 1, 3, 5, 7, 9 or 11, e.g., a subsequence thereof, and/or by introduction of nucleotide substitutions which do not give rise to another amino acid sequence of the polypeptide encoded by the nucleic acid sequence, but which correspond to the codon usage of the host organism intended for production of the protease, or by introduction of nucleotide substitutions which may give rise to a different amino acid sequence. For a general description of nucleotide substitution, see, e.g., Ford et al., 1991, *Protein Expression and Purification* 2: 95-107. Low-allergenic polypeptides can, e.g., be prepared as described above.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for protease activity to identify amino acid residues that are critical to the activity of the molecule. Sites of substrate-protease interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

The present invention also relates to isolated nucleic acid sequences encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with the nucleic acid sequence of either of SEQ ID NO: 1, 3, 5, 7, 9, or 11, preferably the mature peptide encoding parts thereof, or a complementary strand; or an allelic variant; or a subsequence thereof (Sambrook et al., 1989, supra), as defined herein.

The present invention also relates to isolated nucleic acid sequences produced by (a) hybridizing a DNA under very low, low, medium, medium-high, high, or very high stringency conditions with any of the nucleotides mentioned under (i)-(vi) above, preferably the mature peptide encoding parts thereof, or a subsequence, or a complementary strand thereof; and (b) isolating the nucleic acid sequence.

Methods for Producing Mutant Nucleic Acid Sequences

The present invention further relates to methods for producing a mutant nucleic acid sequence, comprising introducing at least one mutation into the mature polypeptide coding parts of either of SEQ ID NO: 1, 3, 5, 7, 9, or 11, or a subsequence thereof, wherein the mutant nucleic acid sequence encodes a polypeptide which consists of the mature peptide of SEQ ID NO: 2, 4, 6, 8, 10, or 12, respectively; or a fragment thereof which has protease activity.

The introduction of a mutation into the nucleic acid sequence to exchange one nucleotide for another nucleotide may be accomplished by site-directed mutagenesis using any of the methods known in the art. Particularly useful is the procedure that utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used.

Nucleic Acid Constructs

The present invention also relates to nucleic acid constructs comprising a nucleic acid sequence of the present invention operably linked to one or more control sequences that direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains all the control sequences required for expression of a coding sequence of the present invention. The term "coding sequence" is defined herein as a nucleic acid sequence that directly specifies the amino acid sequence of its protein product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components that are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence, a nucleic acid sequence that is recognized by a host cell for expression of the nucleic acid sequence. The promoter sequence contains transcriptional control sequences that mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American* 242: 74-94 (1980); and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

Preferred terminators for bacterial host cells, such as a *Bacillus* host cell, are the terminators from *Bacillus licheniformis* alpha-amylase gene (amyL), the *Bacillus stearothermophilus* maltogenic amylase gene (amyM), or the *Bacillus amyloliquefaciens* alpha-amylase gene (amyQ).

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

In a preferred embodiment, the signal peptide coding region is the signal peptide coding region of either of SEQ ID NO: 1, 3, 5, 7, 9, or 11.

In another preferred embodiment, the propeptide coding region is the propeptide coding regions of either of SEQ ID NO: 1, 3, 5, 7, 9, or 11.

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome.

For integration into the host cell genome, the vector may rely on the nucleic acid sequence encoding the polypeptide or any other element of the vector for stable integration of the vector into the genome by homologous or non homologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

The protease may also be co-expressed together with at least one other enzyme of interest for animal feed, such as an amylase; phytase; xylanase; galactanase; alpha-galactosidase; protease, phospholipase; and/or a beta-glucanase. The enzymes may be co-expressed from different vectors, from one vector, or using a mixture of both techniques. When using different vectors, the vectors may have different selectable markers, and different origins of replication. When using only one vector, the genes can be expressed from one or more promoters. If cloned under the regulation of one promoter (di- or multi-cistronic), the order in which the genes are cloned may affect the expression levels of the proteins. The protease may also be expressed as a fusion protein, i.e., that the gene encoding protease has been fused in frame to the gene encoding another protein. This protein may be another enzyme or a functional domain from another enzyme.

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a *Bacillus* cell, or a *Streptomyces* cell, or cells of lactic acid bacteria; or gram negative bacteria such as *E. coli* and *Pseudomonas* sp. Lactic acid bacteria include, but are not limited to, species of the genera *Lactococcus, Lactobacillus, Leuconostoc, Streptococcus, Pediococcus*, and *Enterococcus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be a eukaryote, such as a non-human animal cell, an insect cell, a plant cell, or a fungal cell.

In one particular embodiment, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In another particular embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

The yeast host cell may be a *Candida, Hansenula, Kluyveromyces, Pichia, Saccharomyces, Schizosaccharomyces*, or *Yarrowia* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

Examples of filamentous fungal host cells are cells of species of, but not limited to, *Acremonium, Aspergillus, Fusarium, Humicola, Mucor, Myceliophthora, Neurospora, Penicillium, Thielavia, Tolypocladium*, or *Trichoderma*.

Fungal cells may be transformed by a process involving protoplast formation, transformation of the protoplasts, and regeneration of the cell wall in a manner known per se.

Suitable procedures for transformation of *Aspergillus* host cells are described in EP 238023 and Yelton et al., 1984, *Proceedings of the National Academy of Sciences USA* 81: 1470-1474. Suitable methods for transforming *Fusarium* species are described by Malardier et al., 1989, Gene 78: 147-156 and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp. 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention comprising (a) cultivating a strain, which in its wild-type form is capable of producing the polypeptide, to produce a supernatant comprising the polypeptide; and (b) recovering the polypeptide. In a preferred embodiment, the strain is of the phylum Actinobacteria, preferably of the class Actinobacteria, more preferably of the order Actinomycetales, even more preferably of the family Nocardiopsaceae, and most preferably of the genus *Nocardiopsis*, for example any of the *Nocardiopsis* species, such as the specific strains listed hereinbefore.

The present invention also relates to methods for producing a polypeptide of the present invention comprising (a) cultivating a host cell under conditions conducive for production of the polypeptide; and (b) recovering the polypeptide.

The present invention also relates to methods for producing a polypeptide of the present invention comprising (a) cultivating a host cell under conditions conducive for production of the polypeptide, wherein the host cell comprises a mutant nucleic acid sequence comprising at least one mutation in the mature peptide encoding parts of either of SEQ ID NO: 1, 3, 5, 7, 9, or 11, in which the mutant nucleic acid sequence encodes a polypeptide which (i) consists of the mature peptides of either of SEQ ID NO: 2, 4, 6, 8, 10, or 12, respectively; or (ii) is a variant of any of the sequences of (i), wherein the variant comprises a substitution, deletion, and/or insertion of one or more amino acids, or (iii) is an allelic variant of any of the sequences of (i), or (iv) is a fragment of any of the sequences of (i).

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of a protease product, or disappearance of a protease substrate. For example, a protease assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989).

Plants

The present invention also relates to a transgenic plant, plant part, or plant cell which has been transformed with a nucleic acid sequence encoding a polypeptide having protease activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

In a particular embodiment, the polypeptide is targeted to the endosperm storage vacuoles in seeds. This can be obtained by synthesizing it as a precursor with a suitable signal peptide, see Horvath et al. in *PNAS* 97(4): 1914-1919 (Feb. 15, 2000).

The transgenic plant can be dicotyledonous (a dicot) or monocotyledonous (a monocot) or engineered variants thereof. Examples of monocot plants are grasses, such as meadow grass (blue grass, *Poa*), forage grass such as *Festuca*, *Lolium*, temperate grass, such as *Agrostis*, and cereals, e.g., wheat, oats, rye, barley, rice, sorghum, triticale (stabilized hybrid of wheat (Triticum) and rye (Secale), and maize (corn). Examples of dicot plants are tobacco, legumes, such as sunflower (*Helianthus*), cotton (*Gossypium*), lupins, potato, sugar beet, pea, bean and soybean, and cruciferous plants (family Brassicaceae), such as cauliflower, rape seed, and the closely related model organism *Arabidopsis thaliana*. Low-phytate plants as described, e.g., in U.S. Pat. No. 5,689,054 and U.S. Pat. No. 6,111,168 are examples of engineered plants.

Examples of plant parts are stem, callus, leaves, root, fruits, seeds, and tubers, as well as the individual tissues comprising these parts, e.g., epidermis, mesophyll, parenchyma, vascular tissues, meristems. Also specific plant cell compartments, such as chloroplast, apoplast, mitochondria, vacuole, peroxisomes, and cytoplasm are considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seed coats.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences are determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific cell compartment, tissue or plant part such as seeds or leaves. Regulatory sequences are, for example, described by Tague et al., 1988, *Plant Physiology* 86: 506.

For constitutive expression, the following promoters may be used: The 35S-CaMV promoter (Franck et al., 1980, *Cell* 21: 285-294), the maize ubiquitin 1 (Christensen A H, Sharrock R A and Quail 1992. Maize polyubiquitin genes: structure, thermal perturbation of expression and transcript splicing, and promoter activity following transfer to protoplasts by electroporation), or the rice actin 1 promoter (*Plant Mol. Biol.* 18, 675-689.; Zhang et al., 1991, Analysis of rice Act1 5' region activity in transgenic rice plants. *Plant Cell* 3, 1155-1165). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the *chlorella* virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may be inducible by abiotic treatments such as temperature, drought or alterations in salinity or inducible by exogenously applied substances that activate the promoter, e.g., ethanol, oestrogens, plant hormones like ethylene, abscisic acid, gibberellic acid, and/or heavy metals.

A promoter enhancer element may also be used to achieve higher expression of the protease in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

Still further, the codon usage may be optimized for the plant species in question to improve expression (see Horvath et al. referred to above).

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38), and it can also be used for transforming monocots, although other transformation methods are more often used for these plants. Presently, the method of choice for generating transgenic monocots, supplementing the *Agrobacterium* approach, is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated therein the expression construct are selected and regenerated into whole plants according to methods well-known in the art. Often the transformation procedure is designed for the selective elimination of selection genes either during regeneration or in the following generations by using, e.g., co-transformation with two separate T-DNA constructs or site specific excision of the selection gene by a specific recombinase.

The present invention also relates to methods for producing a polypeptide of the present invention comprising (a) cultivating a transgenic plant or a plant cell comprising a nucleic acid sequence encoding a polypeptide having protease activity of the present invention under conditions conducive for production of the polypeptide; and (b) recovering the polypeptide.

Animals

The present invention also relates to a transgenic, non-human animal and products or elements thereof, examples of which are body fluids such as milk and blood, organs, flesh, and animal cells. Techniques for expressing proteins, e.g., in mammalian cells, are known in the art, see, e.g., the handbook Protein Expression: A Practical Approach, Higgins and Hames (eds), Oxford University Press (1999), and the three other handbooks in this series relating to Gene Transcription, RNA processing, and Post-translational Processing. Generally speaking, to prepare a transgenic animal, selected cells of a selected animal are transformed with a nucleic acid sequence encoding a polypeptide having protease activity of the present invention so as to express and produce the polypeptide. The polypeptide may be recovered from the animal, e.g., from the milk of female animals, or the polypeptide may be expressed to the benefit of the animal itself, e.g., to assist the animal's digestion. Examples of animals are mentioned below in the section headed Animal Feed.

To produce a transgenic animal with a view to recovering protease from the milk of the animal, a gene encoding the protease may be inserted into the fertilized eggs of an animal in question, e.g., by use of a transgene expression vector which comprises a suitable milk protein promoter, and the gene encoding protease. The transgene expression vector is microinjected into fertilized eggs, and preferably permanently integrated into the chromosome. Once the egg begins to grow and divide, the potential embryo is implanted into a surrogate mother, and animals carrying the transgene are identified. The resulting animal can then be multiplied by conventional breeding. The polypeptide may be purified from the animal's milk, see, e.g., Meade, H. M. et al (1999): Expression of recombinant proteins in the milk of transgenic animals, Gene expression systems: Using nature for the art of expression. J. M. Fernandez and J. P. Hoeffler (eds.), Academic Press.

In the alternative, in order to produce a transgenic non-human animal that carries in the genome of its somatic and/or germ cells a nucleic acid sequence including a heterologous transgene construct including a transgene encoding protease, the transgene may be operably linked to a first regulatory sequence for salivary gland specific expression of protease, as disclosed in WO 00/64247.

Compositions

In a still further aspect, the present invention relates to compositions comprising a polypeptide of the present invention.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptides or polypeptide compositions of the invention.

Animal Feed

The present invention is also directed to methods for using the polypeptides having protease activity in animal feed, as well as to feed compositions and feed additives comprising the polypeptides of the invention.

The term animal includes all animals, including human beings. Examples of animals are non-ruminants, and ruminants. Ruminant animals include, for example, animals such as sheep, goats, horses, and cattle, e.g., beef cattle, cows, and young calves. In a particular embodiment, the animal is a non-ruminant animal. Non-ruminant animals include monogastric animals, e.g., pigs or swine (including, but not limited to, piglets, growing pigs, and sows); poultry such as turkeys, ducks and chicken (including but not limited to broiler chicks, layers); young calves; and fish (including but not limited to salmon, trout, tilapia, catfish and carps; and crustaceans (including but not limited to shrimps and prawns).

The term feed or feed composition means any compound, preparation, mixture, or composition suitable for, or intended for intake by an animal.

In the use according to the invention the protease can be fed to the animal before, after, or simultaneously with the diet. The latter is preferred.

In a particular embodiment, the protease, in the form in which it is added to the feed, or when being included in a feed additive, is well-defined. Well-defined means that the protease preparation is at least 50% pure as determined by Size-exclusion chromatography (see Example 12 of WO 01/58275). In other particular embodiments the protease preparation is at least 60, 70, 80, 85, 88, 90, 92, 94, or at least 95% pure as determined by this method.

A well-defined protease preparation is advantageous. For instance, it is much easier to dose correctly to the feed a protease that is essentially free from interfering or contaminating other proteases. The term dose correctly refers in particular to the objective of obtaining consistent and constant results, and the capability of optimising dosage based upon the desired effect.

For the use in animal feed, however, the protease need not be that pure; it may, e.g., include other enzymes, in which case it could be termed a protease preparation.

The protease preparation can be (a) added directly to the feed (or used directly in a protein treatment process), or (b) it can be used in the production of one or more intermediate compositions such as feed additives or premixes that is subsequently added to the feed (or used in a treatment process). The degree of purity described above refers to the purity of the original protease preparation, whether used according to (a) or (b) above.

Protease preparations with purities of this order of magnitude are in particular obtainable using recombinant methods of production, whereas they are not so easily obtained and also subject to a much higher batch-to-batch variation when the protease is produced by traditional fermentation methods.

Such protease preparation may of course be mixed with other enzymes.

In a further particular embodiment, the protease for use according to the invention is capable of solubilizing proteins according to the in vitro model of Example 8 herein.

The protein may be an animal protein, such as meat and bone meal, and/or fish meal; or it may be a vegetable protein.

The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g., soybean, lupine, pea, or bean.

In another particular embodiment, the vegetable protein source is material from one or more plants of the family Chenopodiaceae, e.g., beet, sugar beet, spinach or quinoa.

Other examples of vegetable protein sources are rapeseed, sunflower seed, cotton seed, and cabbage.

Soybean is a preferred vegetable protein source.

Other examples of vegetable protein sources are cereals such as barley, wheat, rye, oat, maize (corn), rice, triticale, and sorghum.

The treatment according to the invention of proteins with at least one protease of the invention results in an increased solubilization of proteins, as compared to the blank. At least 101%, or 102%, 103%, 104%, 105%, 106%, or at least 107% solubilized protein may be obtainable using the proteases of the invention, reference being had to the in vitro model of Example 8 herein. The term solubilization of proteins basically means bringing protein(s) into solution. Such solubilization may be due to protease-mediated release of protein from other components of the usually complex natural compositions such as feed. Solubilization can be measured as an increase in the amount of soluble proteins, by reference to a sample with no protease treatment (see Example 8).

The treatment according to the invention of proteins with at least one protease of the invention results in an increased digestibility of proteins, as compared to the blank. At least 101%, or 102%, 103%, 104%, 105%, 106%, 107%, 108%, 109%, 110%, 111%, 112%, 113%, 114%, 115%, or at least 116% digestible protein may be obtainable using the proteases of the invention, reference being had to the in vitro model of Example 8 herein.

In a particular embodiment of a treatment process the protease(s) in question is affecting (or acting on, or exerting its solubilizing influence on) the proteins, such as vegetable proteins or protein sources. To achieve this, the protein or protein source is typically suspended in a solvent, e.g., an aqueous solvent such as water, and the pH and temperature values are adjusted paying due regard to the characteristics of the enzyme in question. For example, the treatment may take place at a pH-value at which the activity of the actual protease is at least 5%, 10%, 20%, 30%, 40%, 50%, 60%, 70%, 80%, or at least 90%. Likewise, for example, the treatment may take place at a temperature at which the activity of the actual protease is at least 5%, 10%, 20%, 30%, 40%, 50%, 60%, 70%, 80%, or at least 90%. The above percentage activity indications are relative to the maximum activities. The enzymatic reaction is continued until the desired result is achieved, following which it may or may not be stopped by inactivating the enzyme, e.g., by a heat-treatment step.

In another particular embodiment of a treatment process of the invention, the protease action is sustained, meaning, e.g., that the protease is added to the proteins, but its solubilizing influence is so to speak not switched on until later when desired, once suitable solubilizing conditions are established, or once any enzyme inhibitors are inactivated, or whatever other means could have been applied to postpone the action of the enzyme.

In one embodiment the treatment is a pre-treatment of animal feed or proteins for use in animal feed, i.e., the proteins are solubilized before intake.

The term improving the nutritional value of an animal feed means improving the availability of the proteins, thereby leading to increased protein extraction, higher protein yields, and/or improved protein utilisation. The nutritional value of the feed is therefore increased, and the growth rate and/or weight gain and/or feed conversion (i.e., the weight of ingested feed relative to weight gain) of the animal is/are improved.

The protease can be added to the feed in any form, be it as a relatively pure protease, or in admixture with other components intended for addition to animal feed, i.e., in the form of animal feed additives, such as the so-called pre-mixes for animal feed.

In a further aspect the present invention relates to compositions for use in animal feed, such as animal feed, and animal feed additives, e.g., premixes.

Apart from the protease of the invention, the animal feed additives of the invention contain at least one fat-soluble vitamin, and/or at least one water soluble vitamin, and/or at least one trace mineral, and/or at least one macro mineral.

Further, optional, feed-additive ingredients are colouring agents, e.g., carotenoids such as beta-carotene, astaxanthin, and lutein; aroma compounds; stabilisers; antimicrobial peptides; polyunsaturated fatty acids; reactive oxygen generating species; and/or at least one other enzyme selected from amongst phytase (EC 3.1.3.8 or 3.1.3.26); xylanase (EC 3.2.1.8); galactanase (EC 3.2.1.89); alpha-galactosidase (EC 3.2.1.22); protease (EC 3.4.-.-), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); and/or beta-glucanase (EC 3.2.1.4 or EC 3.2.1.6).

In a particular embodiment these other enzymes are well-defined (as defined above for protease preparations).

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are 018, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

Usually fat- and water-soluble vitamins, as well as trace minerals form part of a so-called premix intended for addition to the feed, whereas macro minerals are usually separately added to the feed. Either of these composition types, when enriched with a protease of the invention, is an animal feed additive of the invention.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The following are non-exclusive lists of examples of these components:

Examples of fat-soluble vitamins are vitamin A, vitamin D3, vitamin E, and vitamin K, e.g., vitamin K3.

Examples of water-soluble vitamins are vitamin B12, biotin and choline, vitamin B1, vitamin B2, vitamin B6, niacin, folic acid and panthothenic acid, e.g., Ca-D-panthothenate.

Examples of trace minerals are manganese, zinc, iron, copper, iodine, selenium, and cobalt.

Examples of macro minerals are calcium, phosphorus and sodium. The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

In a still further embodiment, the animal feed additive of the invention comprises at least one of the below vitamins, preferably to provide an in-feed-concentration within the ranges specified in the below table I (for piglet diets, and broiler diets, respectively).

TABLE I

Typical vitamin recommendations

| Vitamin | Piglet diet | Broiler diet |
|---|---|---|
| Vitamin A | 10,000-15,000 IU/kg feed | 8-12,500 IU/kg feed |
| Vitamin D3 | 1800-2000 IU/kg feed | 3000-5000 IU/kg feed |
| Vitamin E | 60-100 mg/kg feed | 150-240 mg/kg feed |
| Vitamin K3 | 2-4 mg/kg feed | 2-4 mg/kg feed |
| Vitamin B1 | 2-4 mg/kg feed | 2-3 mg/kg feed |
| Vitamin B2 | 6-10 mg/kg feed | 7-9 mg/kg feed |
| Vitamin B6 | 4-8 mg/kg feed | 3-6 mg/kg feed |
| Vitamin B12 | 0.03-0.05 mg/kg feed | 0.015-0.04 mg/kg feed |
| Niacin (Vitamin B3) | 30-50 mg/kg feed | 50-80 mg/kg feed |
| Pantothenic acid | 20-40 mg/kg feed | 10-18 mg/kg feed |
| Folic acid | 1-2 mg/kg feed | 1-2 mg/kg feed |
| Biotin | 0.15-0.4 mg/kg feed | 0.15-0.3 mg/kg feed |
| Choline chloride | 200-400 mg/kg feed | 300-600 mg/kg feed |

The present invention also relates to animal feed compositions. Animal feed compositions or diets have a relatively high content of protein. Poultry and pig diets can be characterized as indicated in Table B of WO 01/58275, columns 2-3. Fish diets can be characterized as indicated in column 4 of this Table B. Furthermore such fish diets usually have a crude fat content of 200-310 g/kg.

WO 01/58275 corresponds to U.S. Ser. No. 09/779,334 which is hereby incorporated by reference.

An animal feed composition according to the invention has a crude protein content of 50-800 g/kg, and furthermore comprises at least one protease as claimed herein. Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e., Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein as defined above. It may also contain animal protein, such as Meat and Bone Meal, and/or Fish Meal, typically in an amount of 0-25%.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

Animal diets can, e.g., be manufactured as mash feed (non pelleted) or pelleted feed. Typically, the milled feed-stuffs are mixed and sufficient amounts of essential vitamins and minerals are added according to the specifications for the species in question. Enzymes can be added as solid or liquid enzyme formulations. For example, a solid enzyme formulation is typically added before or during the mixing step; and a liquid enzyme preparation is typically added after the pelleting step. The enzyme may also be incorporated in a feed additive or premix.

The final enzyme concentration in the diet is within the range of 0.01-200 mg enzyme protein per kg diet, for example in the range of 0.5-25 mg enzyme protein per kg animal diet.

The protease should of course be applied in an effective amount, i.e., in an amount adequate for improving solubilization, digestibility, and/or improving nutritional value of feed. It is at present contemplated that the enzyme is administered in one or more of the following amounts (dosage ranges): 0.01-200; 0.01-100; 0.5-100; 1-50; 5-100; 10-100; 0.05-50; or 0.10-10—all these ranges being in mg protease protein per kg feed (ppm).

For determining mg protease protein per kg feed, the protease is purified from the feed composition, and the specific activity of the purified protease is determined using a relevant assay (see under protease activity, substrates, and assays). The protease activity of the feed composition as such is also determined using the same assay, and on the basis of these two determinations, the dosage in mg protease protein per kg feed is calculated.

The same principles apply for determining mg protease protein in feed additives. Of course, if a sample is available of the protease used for preparing the feed additive or the feed, the specific activity is determined from this sample (no need to purify the protease from the feed composition or the additive).

Detergent Compositions

The protease of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the protease of the invention. The detergent additive as well as the detergent composition may comprise one or more other enzymes such as another protease, such as alkaline proteases from *Bacillus*, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258068 and EP 305216 or from *H. insolens* as described in WO 96/13580, a *Pseudomonas* lipase, e.g., from *P. alcaligenes* or *P. pseudoalcaligenes* (EP 218272), *P. cepacia* (EP 331376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, Biochimica et Biophysica Acta 1131: 253-360), *B. stearothermophilus* (JP 64/744992) or *B. pumilus* (WO 91/16422). Other examples are lipase variants such as those described in WO 92/05249, WO 94/01541, EP 407225, EP 260105, WO 95/35381, WO 96/00292, WO 95/30744, WO 94/25578, WO 95/14783, WO 95/22615, WO 97/04079 and WO 97/07202. Preferred commercially available lipase enzymes include Lipolase™ and Lipolase Ultra™ (Novozymes A/S). Suitable amylases (alpha- and/or beta-) include those of bacterial or fungal origin. Chemically modified or protein engineered mutants are included. Amylases include, for example, alpha-amylases obtained from *Bacillus*, e.g., a special strain of *B. lichenifonnis*, described in more detail in GB 1,296,839. Examples of useful amylases are the variants described in WO 94/02597, WO 94/18314, WO 95/26397, WO 96/23873, WO 97/43424, WO 00/60060, and WO 01/66712, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444. Commercially available amylases are Natalase™, Supramyl™, Stainzyme™, Duramyl™, Termamyl™, Fungamyl™ and BAN™ (Novozymes A/S), Rapidase™ and Purastar™ (from Genencor International Inc.).

Suitable cellulases include those of bacterial or fungal origin. Chemically modified or protein engineered mutants are included. Suitable cellulases include cellulases from the genera *Bacillus*, *Pseudomonas*, *Humicola*, *Fusarium*, *Thielavia*, *Acremonium*, e.g., the fungal cellulases produced from *Humicola insolens*, *Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259. Especially suitable cellulases are the alkaline or neutral cellulases having colour care benefits. Examples of such cellulases are cellulases described in EP 0495257, EP 531372, WO 96/11262, WO 96/29397, WO 98/08940. Other examples are cellulase variants such as those described in WO 94/07998, EP 0531315, U.S. Pat. No. 5,457,046, U.S. Pat. No. 5,686,593, U.S. Pat. No. 5,763,254, WO 95/24471, WO 98/12307 and WO 99/01544. Commercially available cellulases include Celluzyme™, and Carezyme™ (Novozymes A/S), Clazinase™, and Puradax HA™ (Genencor International Inc.), and KAC-500(B)™ (Kao Corporation).

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include Guardzyme™ (Novozymes).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, e.g., as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g., SKS-6 from Hoechst).

The detergent may comprise one or more polymers. Examples are carboxymethylcellulose, poly(vinylpyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, e.g., the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, e.g., WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The enzyme of the invention may additionally be incorporated in the detergent formulations disclosed in WO 97/07202.

Particular Embodiments

The invention also relates to the following particular embodiments, in what follows numbered 1-21 and 42-121:

1. An isolated polypeptide having protease activity, selected from the group consisting of: (a) a polypeptide having an amino acid sequence which has a degree of identity to amino acids 1-192 of SEQ ID NO: 4 of at least 69.9%; (b) a polypeptide which is encoded by a nucleic acid sequence which hybridizes under low stringency conditions with (i) nucleotides 574-1149 of SEQ ID NO:3, (ii) a subsequence of (i) of at least 100 nucleotides, and/or (iii) a complementary strand of (i), or (ii); (c) a variant of the polypeptide having an amino acid sequence of amino acids 1-192 of SEQ ID NO: 4 comprising a substitution, deletion, extension, and/or insertion of one or more amino acids; (d) an allelic variant of (a), or (b); and (e) a fragment of (a), (b), or (d) that has protease activity.

2. The polypeptide of embodiment 1 which comprises any one of the following proteases: (a) amino acids 1-192 of SEQ ID NO: 6; (b) amino acids 1-189 of SEQ ID NO: 10; (c) amino acids 1-192 of SEQ ID NO: 2; or (d) amino acids 1-192 of SEQ ID NO: 4.

3. An isolated nucleic acid sequence comprising a nucleic acid sequence which encodes a polypeptide having protease activity, and which (a) encodes the polypeptide of any one of embodiments 1-2; (b) hybridizes under low stringency conditions with (i) nucleotides 574-1149 of SEQ ID NO:3, (ii) a subsequence of (i) of at least 100 nucleotides, and/or (iii) a complementary strand of (i), or (ii); and/or (c) has a degree of identity to nucleotides 574-1149 of SEQ ID NO: 3 of at least 77.7%.

4. The nucleic acid sequence of embodiment 3 which comprises any one of the following protease-encoding nucleic acid sequences: (a) nucleotides 574-1149 of SEQ ID NO: 3; (b) nucleotides 574-1149 of SEQ ID NO: 5; (c) nucleotides 586-1152 of SEQ ID NO: 7; or (d) nucleotides 568-1143 of SEQ ID NO: 1.

5. An isolated nucleic acid sequence produced by (a) hybridizing a DNA under low stringency conditions with (i) nucleotides 574-1149 of SEQ ID NO:3; (ii) a subsequence of (i) of at least 100 nucleotides, or (iii) a complementary strand of (i), or (ii); and (b) isolating the nucleic acid sequence.

6. A nucleic acid construct comprising the nucleic acid sequence of any one of embodiments 3-5 operably linked to one or more control sequences that direct the production of the polypeptide in a suitable expression host.

7. A recombinant expression vector comprising the nucleic acid construct of embodiment 6.

8. A recombinant host cell comprising the nucleic acid construct of embodiment 6 or the vector of embodiment 7.

9. A transgenic plant, or plant part, capable of expressing the polypeptide of any one of embodiments 1-2.

10. A transgenic, non-human animal, or products or elements thereof, being capable of expressing the polypeptide of any one of embodiments 1-2.

11. A method for producing a polypeptide of any one of embodiments 1-2, the method comprising (a) cultivating a recombinant host cell of embodiment 8 to produce a supernatant comprising the polypeptide; and (b) recovering the polypeptide.

12. A method for producing a polypeptide of any one of embodiments 1-2, the method comprising (a) cultivating any one of the following strains: (i) *Nocardiopsis dassonvillei* subsp. *dassonvillei* DSM 43235, (ii) *Nocardiopsis prasina* DSM 15649, (iii) *Nocardiopsis prasina* DSM 14010, or (iv) *Nocardiopsis alkaliphila* DSM 44657; and (b) recovering the polypeptide.

13. Use of at least one protease of any one of embodiments 1-2 (i) in animal feed; (ii) in animal feed additives; (iii) in the preparation of a composition for use in animal feed; (iv) for improving the nutritional value of an animal feed; (v) for increasing digestible and/or soluble protein in animal feed; (vi) for increasing the degree of hydrolysis of proteins in animal diets; and/or (vii) for the treatment of proteins.

14. A method for improving the nutritional value of an animal feed, wherein at least one protease of any one of embodiments 1-2 is added to the feed.

15. An animal feed additive comprising (a) at least one protease of any one of embodiments 1-2; and (b) at least one fat-soluble vitamin, and/or (c) at least one water-soluble vitamin, and/or (d) at least one trace mineral.

16. The animal feed additive of embodiment 15, which further comprises amylase; phytase; xylanase; galactanase; alpha-galactosidase; protease, phospholipase; and/or beta-glucanase.

17. An animal feed having a crude protein content of 50 to 800 g/kg and comprising at least one protease of any one of embodiments 1-2.

18. A method for the treatment of proteins, comprising the step of adding at least one protease of any one of embodiments 1-2 to at least one protein or protein source.

19. The method of embodiment 18, wherein soybean is included amongst the at least one protein source.

20. Use of at least one protease of any one of embodiments 1-2 in detergents.

21. *Nocardiopsis* sp. DSM 16424.

42. An isolated polypeptide having protease activity, selected from the group consisting of: (a) a polypeptide having an amino acid sequence which has a degree of identity to amino acids 1-192 of SEQ ID NO: 2 of at least 75.1%; (b) a polypeptide which is encoded by a nucleic acid sequence which hybridizes under low stringency conditions with (i) nucleotides 568-1143 of SEQ ID NO: 1, (ii) a subsequence of (i) of at least 100 nucleotides, and/or (iii) a complementary strand of (i), or (ii); (c) a variant of the polypeptide having an amino acid sequence of amino acids 1-192 of SEQ ID NO: 2 comprising a substitution, deletion, extension, and/or insertion of one or more amino acids; (d) an allelic variant of (a), or (b); and (e) a fragment of (a), (b), or (d) that has protease activity.

43. The polypeptide of embodiment 42 which comprises any one of the following proteases: (a) amino acids 1-192 of SEQ ID NO: 6; (b) amino acids 1-192 of SEQ ID NO: 2; or (c) amino acids 1-192 of SEQ ID NO: 4.

44. An isolated nucleic acid sequence comprising a nucleic acid sequence which encodes a polypeptide having protease activity, and which (a) encodes the polypeptide of any one of embodiments 42-43; (b) hybridizes under low stringency conditions with (i) nucleotides 568-1143 of SEQ ID NO: 1, (ii) a subsequence of (i) of at least 100 nucleotides, and/or (iii) a complementary strand of (i), or (ii); and/or (c) has a degree of identity to nucleotides 568-1143 of SEQ ID NO: 1 of at least 81.2%.

45. The nucleic acid sequence of embodiment 3 or 44 which comprises any one of the following protease-encoding nucleic acid sequences: (a) nucleotides 574-1149 of SEQ ID NO: 3; (b) nucleotides 574-1149 of SEQ ID NO: 5; or (c) nucleotides 568-1143 of SEQ ID NO: 1.

46. An isolated nucleic acid sequence produced by (a) hybridizing a DNA under low stringency conditions with (i) nucleotides 568-1143 of SEQ ID NO: 1; (ii) a subsequence of (i) of at least 100 nucleotides, or (iii) a complementary strand of (i), or (ii); and (b) isolating the nucleic acid sequence.

47. A nucleic acid construct comprising the nucleic acid sequence of any one of embodiments 44-46 operably linked to one or more control sequences that direct the production of the polypeptide in a suitable expression host.

48. A recombinant expression vector comprising the nucleic acid construct of embodiment 47.

49. A recombinant host cell comprising the nucleic acid construct of embodiment 47 or the vector of embodiment 48.

50. A transgenic plant, or plant part, capable of expressing the polypeptide of any one of embodiments 42-43.

51. A transgenic, non-human animal, or products or elements thereof, being capable of expressing the polypeptide of any one of embodiments 42-43.

52. A method for producing a polypeptide of any one of embodiments 42-43, the method comprising (a) cultivating a recombinant host cell of embodiment 49 to produce a supernatant comprising the polypeptide; and (b) recovering the polypeptide.

53. A method for producing a polypeptide of any one of embodiments 42-43, the method comprising (a) cultivating any one of the following strains: (i) *Nocardiopsis dassonvillei* subsp. *dassonvillei* DSM 43235, (ii) *Nocardiopsis prasina* DSM 15649, or (iii) *Nocardiopsis prasina* DSM 14010; and (b) recovering the polypeptide.

54. Use of at least one protease of any one of embodiments 42-43 (i) in animal feed; (ii) in animal feed additives; (iii) in the preparation of a composition for use in animal feed; (iv) for improving the nutritional value of an animal feed; (v) for increasing digestible and/or soluble protein in animal feed; (vi) for increasing the degree of hydrolysis of proteins in animal diets; and/or (vii) for the treatment of proteins.

55. A method for improving the nutritional value of an animal feed, wherein at least one protease of any one of embodiments 42-43 is added to the feed.

56. An animal feed additive comprising (a) at least one protease of any one of embodiments 42-43; and (b) at least one fat-soluble vitamin, and/or (c) at least one water-soluble vitamin, and/or (d) at least one trace mineral.

57. The animal feed additive of embodiment 56, which further comprises amylase;
phytase; xylanase; galactanase; alpha-galactosidase; protease, phospholipase; and/or beta-glucanase.

58. An animal feed having a crude protein content of 50 to 800 g/kg and comprising at least one protease of any one of embodiments 42-43.

59. A method for the treatment of proteins, comprising the step of adding at least one protease of any one of embodiments 42-43 to at least one protein or protein source.

60. The method of embodiment 59, wherein soybean is included amongst the at least one protein source.

61. Use of at least one protease of any one of embodiments 42-43 in detergents.

62. An isolated polypeptide having protease activity, selected from the group consisting of: (a) a polypeptide having an amino acid sequence which has a degree of identity to amino acids 1-189 of SEQ ID NO: 8 of at least 92.2%; (b) a polypeptide which is encoded by a nucleic acid sequence which hybridizes under low stringency conditions with (i) nucleotides 586-1152 of SEQ ID NO: 7, (ii) a subsequence of (i) of at least 100 nucleotides, and/or (iii) a complementary strand of (i), or (ii); (c) a variant of the polypeptide having an amino acid sequence of amino acids 1-189 of SEQ ID NO: 8 comprising a substitution, deletion, extension, and/or insertion of one or more amino acids; (d) an allelic variant of (a), or (b); and (e) a fragment of (a), (b), or (d) that has protease activity.

63. The polypeptide of embodiment 1 or 62, which comprises amino acids 1-189 of SEQ ID NO: 8.

64. An isolated nucleic acid sequence comprising a nucleic acid sequence which encodes a polypeptide having protease activity, and which (a) encodes the polypeptide of any one of embodiments 62-63; (b) hybridizes under low stringency conditions with (i) nucleotides 586-1152 of SEQ ID NO: 7, (ii) a subsequence of (i) of at least 100 nucleotides, and/or (iii) a complementary strand of (i), or (ii); and/or (c) has a degree of identity to nucleotides 586-1152 of SEQ ID NO: 7 of at least 93.6%.

65. The nucleic acid sequence of embodiment 64 which comprises nucleotides 586-1152 of SEQ ID NO: 7.

66. An isolated nucleic acid sequence produced by (a) hybridizing a DNA under low stringency conditions with (i) nucleotides 586-1152 of SEQ ID NO: 7; (ii) a subsequence of (i) of at least 100 nucleotides, or (iii) a complementary strand of (i), or (ii); and (b) isolating the nucleic acid sequence.

67. A nucleic acid construct comprising the nucleic acid sequence of any one of embodiments 64-66 operably linked to one or more control sequences that direct the production of the polypeptide in a suitable expression host.

68. A recombinant expression vector comprising the nucleic acid construct of embodiment 67.

69. A recombinant host cell comprising the nucleic acid construct of embodiment 67 or the vector of embodiment 68.

70. A transgenic plant, or plant part, capable of expressing the polypeptide of any one of embodiments 62-63.

71. A transgenic, non-human animal, or products or elements thereof, being capable of expressing the polypeptide of any one of embodiments 62-63

72. A method for producing a polypeptide of any one of embodiments 62-63, the method comprising (a) cultivating a recombinant host cell of embodiment 69 to produce a supernatant comprising the polypeptide; and (b) recovering the polypeptide.

73. A method for producing a polypeptide of any one of embodiments 62-63, the method comprising (a) cultivating *Nocardiopsis* sp. DSM 16424; and (b) recovering the polypeptide.

74. Use of at least one protease of any one of embodiments 62-63 (i) in animal feed; (ii) in animal feed additives; (iii) in the preparation of a composition for use in animal feed; (iv) for improving the nutritional value of an animal feed; (v) for increasing digestible and/or soluble protein in animal feed; (vi) for increasing the degree of hydrolysis of proteins in animal diets; and/or (vii) for the treatment of proteins.

75. A method for improving the nutritional value of an animal feed, wherein at least one protease of any one of embodiments 62-63 is added to the feed.

76. An animal feed additive comprising (a) at least one protease of any one of embodiments 62-63; and (b) at least one fat-soluble vitamin, and/or (c) at least one water-soluble vitamin, and/or (d) at least one trace mineral.

77. The animal feed additive of embodiment 76, which further comprises amylase; phytase; xylanase; galactanase; alpha-galactosidase; protease, phospholipase; and/or beta-glucanase.

78. An animal feed having a crude protein content of 50 to 800 g/kg and comprising at least one protease of any one of embodiments 62-63.

79. A method for the treatment of proteins, comprising the step of adding at least one protease of any one of embodiments 62-63 to at least one protein or protein source.

80. The method of embodiment 79, wherein soybean is included amongst the at least one protein source.

81. Use of at least one protease of any one of embodiments 62-63 in detergents.

82. An isolated polypeptide having protease activity, selected from the group consisting of: (a) a polypeptide having an amino acid sequence which has a degree of identity to amino acids 1-189 of SEQ ID NO: 10 of at least 93.2%; (b) a polypeptide which is encoded by a nucleic acid sequence which hybridizes under low stringency conditions with (i) nucleotides 586-1149 of SEQ ID NO: 9, (ii) a subsequence of (i) of at least 100 nucleotides, and/or (iii) a complementary strand of (i), or (ii); (c) a variant of the polypeptide having an amino acid sequence of amino acids 1-189 of SEQ ID NO: 10 comprising a substitution, deletion, extension, and/or insertion of one or more amino acids; (d) an allelic variant of (a), or (b); and (e) a fragment of (a), (b), or (d) that has protease activity.

83. The polypeptide of embodiment 1 or 82 which comprises amino acids 1-189 of SEQ ID NO: 10.

84. An isolated nucleic acid sequence comprising a nucleic acid sequence which encodes a polypeptide having protease activity, and which (a) encodes the polypeptide of any one of embodiments 82-83; (b) hybridizes under low stringency conditions with (i) nucleotides 586-1149 of SEQ ID NO: 9, (ii) a subsequence of (i) of at least 100 nucleotides, and/or (iii) a complementary strand of (i), or (ii); and/or (c) has a degree of identity to nucleotides 586-1149 of SEQ ID NO: 9 of at least 90.3%.

85. The nucleic acid sequence of embodiment 3 or 84 which comprises nucleotides 586-1149 of SEQ ID NO: 9.

86. An isolated nucleic acid sequence produced by (a) hybridizing a DNA under low stringency conditions with (i) nucleotides 586-1149 of SEQ ID NO: 9; (ii) a subsequence of (i) of at least 100 nucleotides, or (iii) a complementary strand of (i), or (ii); and (b) isolating the nucleic acid sequence.

87. A nucleic acid construct comprising the nucleic acid sequence of any one of embodiments 84-86 operably linked to one or more control sequences that direct the production of the polypeptide in a suitable expression host.

88. A recombinant expression vector comprising the nucleic acid construct of embodiment 87.

89. A recombinant host cell comprising the nucleic acid construct of embodiment 87 or the vector of embodiment 88.

90. A transgenic plant, or plant part, capable of expressing the polypeptide of any one of embodiments 82-83.

91. A transgenic, non-human animal, or products or elements thereof, being capable of expressing the polypeptide of any one of embodiments 82-83.

92. A method for producing a polypeptide of any one of embodiments 82-83, the method comprising (a) cultivating a recombinant host cell of embodiment 89 to produce a supernatant comprising the polypeptide; and (b) recovering the polypeptide.

93. A method for producing a polypeptide of any one of embodiments 82-83, the method comprising cultivating *Nocardiopsis alkaliphila* DSM 44657; and recovering the polypeptide.

94. Use of at least one protease of any one of embodiments 82-83 (i) in animal feed; (ii) in animal feed additives; (iii) in the preparation of a composition for use in animal feed; (iv) for improving the nutritional value of an animal feed; (v) for increasing digestible and/or soluble protein in animal feed; (vi) for increasing the degree of hydrolysis of proteins in animal diets; and/or (vii) for the treatment of proteins.

95. A method for improving the nutritional value of an animal feed, wherein at least one protease of any one of embodiments 82-83 is added to the feed.

96. An animal feed additive comprising (a) at least one protease of any one of embodiments 82-83; and (b) at least one fat-soluble vitamin, and/or (c) at least one water-soluble vitamin, and/or (d) at least one trace mineral.

97. The animal feed additive of embodiment 96, which further comprises amylase; phytase; xylanase; galactanase; alpha-galactosidase; protease, phospholipase; and/or beta-glucanase.

98. An animal feed having a crude protein content of 50 to 800 g/kg and comprising at least one protease of any one of embodiments 82-83.

99. A method for the treatment of proteins, comprising the step of adding at least one protease of any one of embodiments 82-83 to at least one protein or protein source.

100. The method of embodiment 99, wherein soybean is included amongst the at least one protein source.

101. Use of at least one protease of any one of embodiments 82-83 in detergents.

102. An isolated polypeptide having protease activity, selected from the group consisting of: (a) a polypeptide having an amino acid sequence which has a degree of identity to amino acids 1-189 of SEQ ID NO: 12 of at least 83.3%; (b) a polypeptide which is encoded by a nucleic acid sequence which hybridizes under low stringency conditions with (i) nucleotides 586-1152 of SEQ ID NO: 11, (ii) a subsequence of (i) of at least 100 nucleotides, and/or (iii) a complementary strand of (i), or (ii); (c) a variant of the polypeptide having an amino acid sequence of amino acids 1-189 of SEQ ID NO: 12 comprising a substitution, deletion, extension, and/or insertion of one or more amino acids; (d) an allelic variant of (a), or (b); and (e) a fragment of (a), (b), or (d) that has protease activity.

103. The polypeptide of embodiment 1 or 102 which comprises amino acids 1-189 of SEQ ID NO: 12.

104. An isolated nucleic acid sequence comprising a nucleic acid sequence which encodes a polypeptide having protease activity, and which (a) encodes the polypeptide of any one of embodiments 102-103; (b) hybridizes under low stringency conditions with (i) nucleotides 586-1152 of SEQ ID NO: 11, (ii) a subsequence of (i) of at least 100 nucleotides, and/or (iii) a complementary strand of (i), or (ii); and/or (c) has a degree of identity to nucleotides 586-1152 of SEQ ID NO: 11 of at least 83.9%.

105. The nucleic acid sequence of embodiment 104 which comprises nucleotides 586-1152 of SEQ ID NO: 11.

106. An isolated nucleic acid sequence produced by (a) hybridizing a DNA under low stringency conditions with (i) nucleotides 586-1152 of SEQ ID NO: 11; (ii) a subsequence of (i) of at least 100 nucleotides, or (iii) a complementary strand of (i), or (ii); and (b) isolating the nucleic acid sequence.

107. A nucleic acid construct comprising the nucleic acid sequence of any one of embodiments 104-106 operably linked to one or more control sequences that direct the production of the polypeptide in a suitable expression host.

108. A recombinant expression vector comprising the nucleic acid construct of embodiment 107.

109. A recombinant host cell comprising the nucleic acid construct of embodiment 107 or the vector of embodiment 108.

110. A transgenic plant, or plant part, capable of expressing the polypeptide of any one of embodiments 102-103.

111. A transgenic, non-human animal, or products or elements thereof, being capable of expressing the polypeptide of any one of embodiments 102-103.

112. A method for producing a polypeptide of any one of embodiments 102-103, the method comprising (a) cultivating a recombinant host cell of embodiment 109 to produce a supernatant comprising the polypeptide; and (b) recovering the polypeptide.

113. A method for producing a polypeptide of any one of embodiments 102-103, the method comprising cultivating *Nocardiopsis lucentensis* DSM 44048, and recovering the polypeptide.

114. Use of at least one protease of any one of embodiments 102-103 (i) in animal feed; (ii) in animal feed additives; (iii) in the preparation of a composition for use in animal feed; (iv) for improving the nutritional value of an animal feed; (v) for increasing digestible and/or soluble protein in animal feed; (vi) for increasing the degree of hydrolysis of proteins in animal diets; and/or (vii) for the treatment of proteins.

115. A method for improving the nutritional value of an animal feed, wherein at least one protease of any one of embodiments 102-103 is added to the feed.

116. An animal feed additive comprising (a) at least one protease of any one of embodiments 102-103; and (b) at least one fat-soluble vitamin, and/or (c) at least one water-soluble vitamin, and/or (d) at least one trace mineral.

117. The animal feed additive of embodiment 116, which further comprises amylase; phytase; xylanase; galactanase; alpha-galactosidase; protease, phospholipase; and/or beta-glucanase.

118. An animal feed having a crude protein content of 50 to 800 g/kg and comprising at least one protease of any one of embodiments 102-103.

119. A method for the treatment of proteins, comprising the step of adding at least one protease of any one of embodiments 102-103 to at least one protein or protein source.

120. The method of embodiment 119, wherein soybean is included amongst the at least one protein source.

121. Use of at least one protease of any one of embodiments 102-103 in detergents.

Deposit of Biological Material

The following biological materials have been deposited under the terms of the Budapest Treaty with the DSMZ (Deutsche Sammlung von Mikroorganismen and Zellkulturen GmbH, Mascheroder Weg 1b, D-38124 Braunschweig, Germany), and given the following accession numbers:

| Deposit | Accession Number | Date of Deposit |
|---|---|---|
| *Nocardiopsis* sp. | DSM 16424 | May 24, 2004 |
| *Nocardiopsis prasina* | DSM 15649 | May 30, 2003 |
| *Nocardiopsis prasina* (previously *alba*) | DSM 14010 | Jan. 20, 2001 |

These strains have been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

Strain DSM 15649 was isolated in 2001 from a soil sample from Denmark.

The following strains are publicly available from DSMZ:

| *Nocardiopsis dassonvillei* subsp. *dassonvillei* | DSM 43235 |
|---|---|
| *Nocardiopsis alkaliphila* | DSM 44657 |
| *Nocardiopsis lucentensis* | DSM 44048 |

*Nocardiopsis dassonvillei* subsp. *dassonvillei* strain DSM 43235 was also deposited at other depositary institutions as follows: ATCC 23219, IMRU 1250, NCTC 10489.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

EXAMPLES

Example 1

Cloning and Expression of Three Proteases (L1a, L1b, and L1c)

Reagents and Media

| LB agar | Described in Ausubel, F. M. et al. (eds.) "Current protocols in Molecular Biology" John Wiley and Sons, 1995; |
|---|---|
| LB-PG agar | LB agar supplemented with 0.5% Glucose and 0.05M potassium phosphate, pH 7.0 |
| PS-1 | 10% sucrose, 4% soybean flour, 1% $Na_3PO_4$—$12H_2O$, 0.5% $CaCO_3$, and 0.01% pluronic acid |
| TE | 10 mM Tris-HCl, pH 7.4 1 mM EDTA, pH 8.0 |
| TEL | 50 mg/ml Lysozym in TE-buffer |
| Thiocyanate | 5M guanidium thiocyanate 100 mM EDTA 0.6% w/v N-laurylsarcosine, sodium salt 60 g thiocyanate, 20 ml 0.5M EDTA, pH 8.0, 20 ml $H_2O$ dissolves at 65° C. Cool down to room temperature (RT) and add 0.6 g N-laurylsarcosine. Add $H_2O$ to 100 ml and filter it through a 0.2µ sterile filter. |
| $NH_4Ac$ | 7.5M $CH_3COONH_4$ |
| TER | 1 µg/ml RNAse A in TE-buffer |
| CIA | Chloroform/isoamyl alcohol 24:1 |

Fermentation of *Nocardiopsis* strains

Each of the strains *Nocardiopsis dassonvillei* subsp. *dassonvillei* DSM 43235, *Nocardiopsis prasina* DSM 15649, and *Nocardiopsis prasina* (previously alba) DSM 14010 were grown for 3 days before harvest, in the following medium at 30° C.:

| Trypticase | 20 g |
|---|---|
| Yeast extract | 5 g |
| Ferrochloride | 6 mg |
| Magnesium sulfate | 15 mg |
| Distilled water ad | 1000 ml | pH adjusted to 9 by addition of sodium carbonate.

Preparation of Genomic DNA

Genomic DNA was isolated according to the following procedure:

1. Harvest 1.5 ml culture and re-suspend in 100 µl TEL. Incubate at 37° C. for 30 min.

2. Add 500 µl thiocyanate buffer and leave at room temperature for 10 min.

3. Add 250 µl $NH_4Ac$ and leave at ice for 10 min.

4. Add 500 µl CIA and mix.

5. Transfer to a micro-centrifuge and spin for 10 min. at full speed.

6. Transfer supernatant to a new Eppendorf tube and add 0.54 volume cold isopropanol.

Mix thoroughly.

7. Spin and wash the DNA pellet with 70% EtOH.

8. Re-suspend the genomic DNA in 100 µl TER.

Construction of *Bacillus subtilis* Expression Strains Sav-L1a, Sav-L1b and Sav-L1c The coding region for the pro-mature protease L1a (nucleotides 88-1143 of SEQ ID NO: 1) was amplified with the following primers 1424 and 1485 on genomic DNA isolated from *Nocardiopsis dassonvillei* subsp. *dassonvillei* DSM 43235:

Primer 1485 (SEQ ID NO: 14):
5'-gctttagttcatcgatcgcatcggctgcgaccgtaccggccgagc cag-3'

Primer 1424 (SEQ ID NO: 15):
5'-ggagcggattgaacatgcgattactaaccggtcaccagggacagc c-3'

The coding region for the pro-mature protease L1b (nucleotides 88-1149 of SEQ ID NO: 3) was amplified with the following primers 1751 and 1753 on genomic DNA isolated from *Nocardiopsis prasina* DSM15649:

1751 (SEQ ID NO: 16):
5'-gttcatcgatcgcatcggctgtcaccgcacccaccgagcc-3'

1753 (SEQ ID NO: 17):
5'-ggagcggattgaacatgcgattagctggtgacgaggctgaggttc-3'

The coding region for the pro-mature protease L1c (nucleotides 88-1149 of SEQ ID NO: 5) was amplified with the following primers 1755 and 1756 on genomic DNA isolated from *Nocardiopsis prasina* DSM14010:

1755 (SEQ ID NO: 18):
5'-gttcatcgatcgcatcggctgtgaccgccccgccgag-3'

1756 (SEQ ID NO: 19):
5'-ggagcggattgaacatgcgattagctcgtgacgaggctgaggttc-3'

Each of these L1a, L1b, and L1c polynucleotides were fused, by PCR, in frame to a heterologous DNA fragment encoding a Sav signal peptide (SEQ ID NO: 13).

*Bacillus subtilis* strains designated Sav-L1a, Sav-L1b, and Sav-L1c, respectively, were constructed by incorporating these genes (including the signal peptide encoding part) by homologous recombination on the *Bacillus subtilis* MB1053 host cell genome (WO 03/95658). The genes were expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence. The gene coding for Chloramphenicol acetyltransferase was used as marker (described in, e.g., Diderichsen et al., 1993, A useful cloning vector for *Bacillus subtilis*. *Plasmid* 30:312).

Chloramphenicol resistant transformants were checked for protease activity on 1% skim milk LB-PG agar plates (supplemented with 6 µg/ml chloramphenicol). Some protease positive colonies were further analyzed by DNA sequencing of the insert to confirm the correct DNA sequence, and one strain for each construct was selected.

Fermentation of *Bacillus* Host Strains

Each of the transformed *Bacillus subtilis* host strains were fermented on a rotary shaking table (250 r.p.m.) in 500 ml baffled Erlenmeyer flasks containing 100 ml PS-1 medium supplemented with 6 µg/ml chloramphenicol, at 37° C. for 16 hours, and at 26° C. for extra 4 days.

Example 2

Cloning and Expression of Protease L2a

The pro-form of a protease encoding gene (nucleotides 88-1152 of SEQ ID NO: 7) was isolated from *Nocardiopsis* sp. DSM 16424 by the procedure described in Example 1, except for the use of the following primers:

1718 (SEQ ID NO: 20):
5'-gttcatcgatcgcatcggctgcgcccggccccgtccccag-3'

1720 (SEQ ID NO: 21):
5'-ggagcggattgaacatgcgatcagctggtgcggatgcgaac-3'.

The corresponding protease (SEQ ID NO: 8) was designated L2a.

A *Bacillus subtilis* host strain designated Sav-L2a was constructed, as also generally described in Example 1, and a chloramphenicol resistant, protease-positive colony selected and analyzed by DNA sequencing of the insert.

Example 3

Cloning of Two Additional Proteases

The pro-forms of two additional protease encoding genes (nucleotides 88-1149 of SEQ ID NO: 9, and nucleotides 88-1152 of SEQ ID NO: 11, respectively) were isolated from *Nocardiopsis alkaliphila* DSM 44657, and from *Nocardiopsis lucentensis* DSM 44048, respectively, by the procedure described in Example 1, except for the use of primers 1728 and 1763; and 1747 and 1749, respectively:

1728 (SEQ ID NO: 22):
5'-gttcatcgatcgcatcggctgccccgccccccagtc-3'

1763 (SEQ ID NO: 23):
5'-ggagcggattgaacatgcgattaggtgcgcagacgcaggcccca-3';

1747 (SEQ ID NO: 24):
5'-gttcatcgatcgcatcggctggaaccgtacccacccccagg-3'

1749 (SEQ ID NO: 25):
5'-ggagcggattgaacatgcgattagctggtgcgcagtcgcac-3'

The corresponding proteases (SEQ ID NO: 10 and 12, respectively) were designated L2b, and L2c, respectively.

*Bacillus subtilis* host strains designated Sav-L2b and Sav-L2c, respectively, are constructed, as also generally described in Example 1, and chloramphenicol resistant, protease-positive colonies are selected and analyzed by DNA sequencing of the inserts.

Example 4

Purification and Characterization of the L1a Protease

Protease Assays
1) pNA Assay:
pNA substrate: Suc-AAPF-pNA (Bachem L-1400).
Temperature: Room temperature (25° C.)
Assay buffers: 100 mM succinic acid, 100 mM HEPES, 100 mM CHES, 100 mM CABS, 1 mM $CaCl_2$, 150 mM KCl, 0.01% Triton X-100 adjusted to pH-values 2.0, 2.5, 3.0, 3.5, 4.0, 5.0, 6.0, 7.0, 8.0, 9.0, 10.0, 11.0, and 12.0 with HCl or NaOH.

20 µl protease (diluted in 0.01% Triton X-100) is mixed with 100 µl assay buffer. The assay is started by adding 100 µl pNA substrate (50 mg dissolved in 1.0 ml DMSO and further diluted 45× with 0.01% Triton X-100). The increase in $OD_{405}$ is monitored as a measure of the protease activity.
2) Protazyme AK Assay:
Substrate: Protazyme AK tablet (cross-linked and dyed casein; from Megazyme)
Temperature: controlled (assay temperature).
Assay buffers: 100 mM succinic acid, 100 mM HEPES, 100 mM CHES, 100 mM CABS, 1 mM $CaCl_2$, 150 mM KCl, 0.01% Triton X-100 adjusted to pH-values 2.0, 2.5, 3.0, 3.5, 4.0, 5.0, 6.0, 7.0, 8.0, 9.0, 10.0 and 11.0 with HCl or NaOH.

A Protazyme AK tablet is suspended in 2.0 ml 0.01% Triton X-100 by gentle stirring. 500 µl of this suspension and 500 µl assay buffer are mixed in an Eppendorf tube and placed on ice. 20 µl protease sample (diluted in 0.01% Triton X-100)

is added. The assay is initiated by transferring the Eppendorf tube to an Eppendorf thermomixer, which is set to the assay temperature. The tube is incubated for 15 minutes on the Eppendorf thermomixer at its highest shaking rate (1400 rpm). The incubation is stopped by transferring the tube back to the ice bath. Then the tube is centrifuged in an icecold centrifuge for a few minutes and 200 µl supernatant is transferred to a microtiter plate. $OD_{650}$ is read as a measure of protease activity. A buffer blind is included in the assay (instead of enzyme).

Purification

The transformed *Bacillus* host expressing the L1a protease described in Example 1 was fermented as also described in Example 1, but at 26° C. for 6 days. The culture broth was centrifuged (20000×g, 20 min) and the supernatants were carefully decanted from the precipitates. The combined supernatants were filtered through a Seitz EKS plate in order to remove the rest of the *Bacillus* host cells. The EKS filtrate was transferred to 50 mM $H_3BO_3$, 5 mM succinic acid, 1 mM $CaCl_2$, pH 7 on a G25 sephadex column. Solid ammonium sulfate was added to the enzyme solution from the G25 sephadex column to give a 1.6 M final $(NH_4)_2SO_4$ concentration in the enzyme solution. The enzyme solution was mixed gently with a magnetic stirrer during the $(NH_4)_2SO_4$ addition and the stirring was continued for 30 minutes after the addition to bring the system in equilibrium. Then the enzyme solution was applied to a Butyl Toyopearl column equilibrated in 100 mM $H_3BO_3$, 10 mM succinic acid, 2 mM $CaCl_2$, 1.6 M $(NH_4)_2SO_4$, pH 7. After washing the column extensively with the equilibration buffer, the protease was eluted with a linear $(NH_4)_2SO_4$ gradient (1.6 to 0 M) in the same buffer. Protease containing fractions were pooled and transferred to 20 mM HEPES, pH 8 on a G25 sephadex column and applied to a Q sepharose FF column equilibrated in the same buffer. After washing the column extensively with the equilibration buffer, the protease was eluted with a linear NaCl gradient (0 to 0.5 M) in the same buffer. Fractions from the column were analysed for protease activity (using the Suc-AAPF-pNA assay at pH 9) and active fractions were further analysed by SDS-PAGE. Fractions with only one band (as judged by a coomassie stained SDS-PAGE gel) were pooled to provide the purified preparation which was used for further characterization.

The L1a protease was characterized as described below, in comparison with the other protease derived from *Nocardiopsis dassonvillei* subsp. *dassonvillei* DSM 43235, prepared as described in WO 2004/111220 (in what follows for short designated "the L2 protease").

pH-activity, pH-stability, and Temperature-Activity

The pNA assay was used for obtaining the pH-activity profile as well as the pH-stability profile. For the pH-stability profile the protease was diluted 10× in the assay buffers and incubated for 2 hours at 37° C. After incubation the protease samples were transferred to the same pH (pH 9), before assay for residual activity, by dilution in the pH 9 assay buffer. The Protazyme AK assay was used for obtaining the temperature-activity profile at pH 9. The results are shown in Tables 1-3 below.

TABLE 1 pH-activity profile

| pH | L1a protease | L2 protease |
|---|---|---|
| 2 | 0.00 | 0.00 |
| 3 | 0.00 | 0.00 |

TABLE 1-continued pH-activity profile

| pH | L1a protease | L2 protease |
|---|---|---|
| 4 | 0.02 | 0.03 |
| 5 | 0.10 | 0.11 |
| 6 | 0.25 | 0.21 |
| 7 | 0.38 | 0.37 |
| 8 | 0.66 | 0.71 |
| 9 | 0.97 | 0.97 |
| 10 | 1.00 | 1.00 |
| 11 | 0.99 | 0.94 |
| 12 | 0.94 | — |

TABLE 2 pH-stability profile

| pH | L1a protease | L2 protease |
|---|---|---|
| 2.0 | 0.50 | 1.00 |
| 2.5 | 0.81 | 0.95 |
| 3.0 | 0.93 | 0.97 |
| 3.5 | 0.94 | 1.01 |
| 4.0 | 0.97 | 0.98 |
| 5.0 | 0.96 | 0.97 |
| 6.0 | 0.95 | 0.98 |
| 7.0 | 0.99 | 0.96 |
| 8.0 | 0.97 | 0.99 |
| 9.0 | 0.93 | 0.99 |
| 10.0 | 0.94 | 0.96 |
| 11.0 | 0.94 | 0.94 |
| 12.0 | 0.92 | 0.84 |
| 9.0 and after 2 hours at 5° C. | 1.00 | 1.00 |

TABLE 3

Temperature activity profile

| temperature (° C.) | L1a protease | L2 protease |
|---|---|---|
| 15 | 0.11 | 0.01 |
| 25 | 0.17 | 0.01 |
| 37 | 0.30 | 0.03 |
| 50 | 0.58 | 0.09 |
| 60 | 0.90 | 0.19 |
| 70 | 1.00 | 0.63 |
| 80 | 0.34 | 1.00 |
| 90 | — | 0.35 |

Other Characteristics

The L1a protease is an alpha-lytic protease like enzyme (peptidase family S1E, old notation S2A) which is found to be inhibited by Phenyl Methyl Sulfonyl Fluoride (PMSF), and by the *Streptomyces* Subtilisin Inhibitor (SSI). Its relative molecular weight as determined by SDS-PAGE is $M_r$=22 kDa, and the N-terminal sequence: ADIVGGEAY (SEQ ID NO: 26).

Example 5

Specific Activity of the L1a Protease

The purified protease preparation described in Example 4 was used for determination of the specific activity. The purity of the preparation was above 95% when analysed by SDS-PAGE (determined as described in Example 2A in WO 01/58275). The protease sample was divided in two. One part was analyzed for protein content (mg/ml) by amino acid analysis, the other part was analysed for protease activity.

Amino Acid Analysis (AAA)/(mq/ml)

The peptide bonds of the protease sample were subjected to acid hydrolysis, followed by separation and quantification of the released amino acids on a Biochrom 20 Plus Amino Acid Analyser, commercially available from Bie & Berntsen A/S, Sandbaekvej 5-7, DK-2610 Roedovre, Denmark, according to the manufacturer's instructions. For the acid hydrolysis, the protein sample was dried in a vacuum centrifuge, resolved in 18.5% (vol/vol) HCl+0.1% (vol/vol) phenol and incubated for 16 hr at 110° C. After incubation, the sample was again dried in the vacuum centrifuge, resolved in loading buffer (0.2 M Na-Citrate, pH 2.2) and loaded onto the Biochrom 20 Plus Amino Acid Analyser.

For the quantification, the hydrolysed sample was loaded onto a column of the cation-exchange resin UltroPac no. 8, Sodium-form, which is commercially available from Bie & Berntsen A/S, catalogue no. 80-2104-15. Buffers of varying pH (pH 1 to pH 8) and ionic strength were pumped through the column according to the manufacturer's instructions referred to above, to separate the various amino acids. The column temperature was accurately controlled, also according to the manufacturer's instructions (from 53° C. to 92° C. and back to 53° C.) in order to ensure the required separation. The column eluent was mixed with ninhydrin reagent (Bie & Berntsen, catalogue no. 80-2038-07) and the mixture passed through the high temperature reaction coil of the Amino Acid Analyser. In the reaction coil, ninhydrin reacted with the amino acids to form coloured compounds, the amount of which was directly proportional to the quantity of amino acid present.

Protease Activity Assay (AU/ml)

Denatured haemoglobin (0.65% (w/w) in 6.7 mM $KH_2PO_4$/NaOH buffer, pH 7.50) was degraded at 25° C. for 10 minutes by the protease, and undigested haemoglobin was precipitated with trichloroacetic acid (TCA) and removed by filtration. The TCA-soluble haemoglobin degradation products in the filtrate were determined with Folin & Ciocalteu's phenol reagent, which gives a blue colour with several amino acids. The activity unit (AU) was measured and defined by reference to an ALCALASE™ standard. A detailed description of the assay, as well as a sample of the ALCALASE™ standard, is available on request from Novozymes NS, Krogshoejvej 36, DK-2880 Bagsvaerd, Denmark (assay no. EB-SM-0349.02/01).

The specific activity was calculated as: Specific activity (AU/g)=(Activity (AU/ml)/AAA (mg/ml))×1000 (mg/g).

The specific activity of the L1a protease was 49.8 AU/g, as compared to the specific activity of the protease derived from *Nocardiopsis* sp. NRRL 18262 of 38.3 AU/g.

Example 6

Purification and Characterization of the L2a Protease

The transformed *Bacillus* host expressing the L2a protease described in Example 2 was fermented as described in Example 1, but at 30° C. for 5 days. The culture broth was centrifuged (20000×g, 20 min) and the supernatants were carefully decanted from the precipitates. The combined supernatants were filtered through a Seitz EKS plate in order to remove the rest of the *Bacillus* host cells. The EKS filtrate was transferred to 50 mM $H_3BO_3$, 5 mM succinic acid, 1 mM $CaCl_2$, pH 7 on a G25 sephadex column and applied to a bacitracin silica column equilibrated in the same buffer. After washing the bacitracin column extensively with the equilibration buffer, the protease was step-eluted with 100 mM $H_3BO_3$, 10 mM succinic acid, 2 mM $CaCl_2$, 1 M NaCl, 25% isopropanol, pH 7. The bacitracin eluate was transferred to 50 mM $H_3BO_3$, 10 mM $CH_3COOH$, 1 mM $CaCl_2$, pH 4.5 on a G25 sephadex column and applied to a S sepharose HP column equilibrated in the same buffer. After washing the column extensively with the equilibration buffer, the protease was eluted with a linear NaCl gradient (0 to 0.5 M) in the same buffer. Fractions from the column were analysed for protease activity (using the Protazyme AK assay at 37° C. and pH 9) and active fractions were further analysed by SDS-PAGE. Fractions with only one band was (as judged by a coomassie stained SDS-PAGE gel), were pooled to provide the purified preparation which was used for further characterization.

The L2a protease was characterized as described in Example 4 above, in comparison with a known protease derived from *Nocardiopsis* sp. NRRL 18262 (for short designated "Protease 10"). The results are shown in Tables 4-6 below.

TABLE 4 pH-activity profile

| pH | L2a protease | Protease 10 |
|---|---|---|
| 2 | 0.00 | — |
| 3 | 0.00 | 0.00 |
| 4 | 0.02 | 0.02 |
| 5 | 0.10 | 0.07 |
| 6 | 0.22 | 0.21 |
| 7 | 0.41 | 0.44 |
| 8 | 0.75 | 0.67 |
| 9 | 0.97 | 0.88 |
| 10 | 0.99 | 1.00 |
| 11 | 1.00 | 0.93 |
| 12 | 0.85 | — |

TABLE 5 pH-stability profile

| pH | L2a protease | Protease 10 |
|---|---|---|
| 2.0 | 0.67 | 0.78 |
| 2.5 | 0.93 | 1.00 |
| 3.0 | 0.95 | 1.03 |
| 3.5 | 0.96 | 0.98 |
| 4.0 | 0.97 | 0.99 |
| 5.0 | 0.94 | 1.02 |
| 6.0 | 0.95 | 1.00 |
| 7.0 | 0.97 | 1.01 |
| 8.0 | 0.96 | 0.98 |
| 9.0 | 0.95 | 0.99 |
| 10.0 | 0.96 | 0.99 |
| 11.0 | 0.90 | 0.86 |
| 12.0 | 0.60 | — |
| 9.0 and after 2 hours at 5° C. | 1.00 | 1.00 |

TABLE 6

Temperature activity profile

| Temperature (° C.) | L2a protease | Protease 10 |
|---|---|---|
| 15 | 0.02 | 0.02 |
| 25 | 0.02 | 0.02 |
| 37 | 0.05 | 0.07 |
| 50 | 0.13 | 0.20 |
| 60 | 0.31 | 0.51 |
| 70 | 0.79 | 1.00 |
| 80 | 1.00 | 0.39 |
| 90 | 0.28 | — |

Other Characteristics

The L2a protease is an alpha-lytic protease like enzyme (peptidase family S1E, old notation S2A) which is found to be inhibited by Phenyl Methyl Sulfonyl Fluoride (PMSF). Its relative molecular weight as determined by SDS-PAGE is $M_r=20$ kDa, and the N-terminal sequence: ANIIGGLAYT (SEQ ID NO: 27).

Example 7

Melting Temperature of the L2a Protease

Differential Scanning Calorimetry (DSC)

DSC was used to determine temperature stability at pH 7.0 of the L2a protease derived from Nocardiopsis sp. DSM 16424. The protease was purified as described in Example 6 and dialysed over night at 4° C. against 10 mM sodium phosphate, 50 mM sodium chloride, pH 7.0 and run on a VP-DSC instrument (Micro Cal) with a constant scan rate of 1.5° C./min from 20 to 100° C. Data-handling was performed using the MicroCal Origin software.

The resulting denaturation or melting temperature ($T_m$ or $T_d$), was 78.2° C. The $T_m$ for Protease 10 is 76.5° C.

Example 8

Performance of the L2a Protease in a Monogastric In Vitro Digestion Model

The performance of the purified L2a protease described in Example 6 was tested in an in vitro model simulating the digestion in monogastric animals, in comparison with the known protease derived from Nocardiopsis sp. NRRL 18262 ("Protease 10"). In particular, the protease was tested for its ability to improve solubilization and digestion of maize/-SBM (maize/-soybean meal) proteins. The in vitro system consisted of 18 flasks in which maize/-SBM substrate was initially incubated with HCl/pepsin—simulating gastric digestion—and subsequently with pancreatin—simulating intestinal digestion. Eight of the flasks were dosed with the protease at the start of the gastric phase whereas the remaining ten flasks served as blanks. At the end of the intestinal incubation phase samples of in vitro digesta were removed and analyzed for solubilized and digested protein.

Outline of In Vitro Digestion Procedure

| Components added | pH | Temperature | Time course | Simulated digestion phase |
|---|---|---|---|---|
| 10 g maize/-SBM substrate (6:4), 41 ml HCl (0.105M) | 3.0 | 40° C. | t = 0 min | Mixing |
| 5 ml HCl (0.105M)/pepsin (3000 U/g substrate), 1 ml protease (to provide 100 mg protease enzyme protein per kg of substrate) | 3.0 | 40° C. | t = 30 min | Gastric digestion |
| 16 ml H₂O | 3.0 | 40° C. | t = 1.0 hour | Gastric digestion |
| 7 ml NaOH (0.39M) | 6.8 | 40° C. | t = 1.5 hours | Intestinal digestion |
| 5 ml NaHCO₃ (1M)/pancreatin (8 mg/g diet) | 6.8 | 40° C. | t = 2.0 hours | Intestinal digestion |
| Terminate incubation | 7.0 | 40° C. | t = 6.0 hours | |

Conditions

Substrate: 4 g SBM, 6 g maize (premixed)
ph: 3.0 stomach step/6.8-7.0 intestinal step
HCl: 0.105 M for 1.5 hours (i.e., 30 min HCl-substrate pre-mixing)
pepsin: 3000 U/g diet for 1 hour
pancreatin: 8 mg/g diet for 4 hours
temperature: 40° C.
Replicates: n
Solutions
0.39 M NaOH
0.105 M HCl
0.105 M HCl containing 6000 U pepsin per 5 ml
1 M NaHCO₃ containing 16 mg pancreatin per ml
125 mM NaAc-buffer, pH 6.0
Enzyme Protein Determinations The amount of protease enzyme protein (EP) is calculated on the basis of the $A_{280}$ values and the amino acid sequences (amino acid compositions) using the principles outlined in Gill & von Hippel, 1989, Analytical Biochemistry 182: 319-326.

Experimental Procedure for In Vitro Model

The experimental procedure was according to the above outline. pH was measured at time 1, 2.5, and 5.5 hours. Incubations were terminated after 6 hours and samples of 30 ml were removed and placed on ice before centrifugation (10000×g, 10 min, 4° C.). Supernatants were removed and stored at −20° C.

Analysis

All samples were analyzed for content of solubilized and digested protein using gel filtration.

Estimation of Solubilized and Digested Protein

The content of solubilized protein in supernatants from in vitro digested samples was estimated by quantifying crude protein (CP) using gel filtration HPLC. Supernatants were thawed, filtered through 0.45 µm polycarbonate filters and diluted (1:50, v/v) with H₂O. Diluted samples were chromatographed by HPLC using a Superdex Peptide PE (7.5× 300 mm) gel filtration column (Global). The eluent used for isocratic elution was 50 mM sodium phosphate buffer (pH 7.0) containing 150 mM NaCl. The total volume of eluent per run was 26 ml and the flow rate was 0.4 ml/min. Elution profiles were recorded at 214 nm and the total area under the profiles was determined by integration. To estimate protein content from integrated areas, a calibration curve ($R^2=0.9993$) was made from a dilution series of an in vitro digested reference maize/-SBM sample with known total protein content. The protein determination in this reference sample was carried out using the Kjeldahl method (determination of % nitrogen; A.O.A.C. (1984) Official Methods of Analysis 14th ed., Washington D.C.).

The content of digested protein was estimated by integrating the chromatogram area corresponding to peptides and amino acids having a molecular mass of 1500 Dalton or below (Savoie et al., 1986, Dialysis Cell For The In-vitro Measurement Of Protein Digestibility. J. Food Sci. 51, 494-498; Babinszky et al., 1990, An In-vitro Method for Prediction of The Digestible Crude Protein Content in Pig Feeds. J. Sci. Food Agr. 50: 173-178; Boisen et al., 1991, Critical Evaluation of In-vitro Methods for Estimating Digestibility in Simple-Stomach Animals. Nutrition Research Reviews 4: 141-162). To determine the 1500 Dalton dividing line, the gel filtration column was calibrated using cytochrome C (Boehringer, Germany), aprotinin, gastrin I, and substance P (Sigma Aldrich, USA), as molecular mass standards.

Results

The results shown in Table 7 below indicate that the L2a protease, like Protease 10, significantly increased the level of soluble and digestible protein relative to the blank. Furthermore, the L2a protease appears to at least numerically improve the level of digestible protein as compared to the known Protease 10.

TABLE 7

Solubilized and digested crude protein

Relative to blank

| Enzyme | N | % digestible CP | | CV % | % soluble CP | | CV % |
|---|---|---|---|---|---|---|---|
| Blank | 10 | 100.0 | a | 5.5 | 100.0 | a | 4.4 |
| L2a protease | 3 | 116.1 | b | 0.7 | 107.2 | b | 1.1 |
| Protease 10 | 5 | 112.1 | b | 1.0 | 110.2 | b | 0.6 |

Different letters within the same column indicate significant differences (1-way ANOVA, Tukey-Kramer test, P < 0.05). SD = Standard Deviation. % CV = Coefficient of Variance = (SD/mean value) × 100%

Example 9

Animal Feed and Animal Feed Additives

An animal feed additive comprising protease L2a of the invention, in the form of a vitamins and mineral premix, is composed as shown in Table 8 below. The vitamins and the carotenoids are commercially available from DSM Nutritional Products. All amounts are in g/kg.

TABLE 8

| Premix composition | | |
|---|---|---|
| Vitamin A | ROVIMIX A 500 | 4.00 |
| Vitamin D3 | ROVIMIX D3 500 | 1.00 |
| Vitamin E | ROVIMIX E 50 Ads | 8.00 |
| Vitamin B2 | ROVIMIX B2 80-SD | 1.0 |
|  | CAROPHYLL Yellow | 10.0 |
|  | Choline chloride 50%, min. | 300.0 |
| Minerals | Mn Oxide | 60.0 |
|  | Zn Oxide | 12.0 |
|  | Fe Sulphate monohydrate | 20.0 |
|  | Cu Oxide | 2.0 |
|  | Co Sulphate | 0.2 |
| Enzyme | Protease L2a (enzyme protein) | 10.0 |
|  | Wheat middlings | 571.8 |

The Premix of Table 8 is included in a diet for layers with a composition as shown in Table 9 below. The amount of each ingredient is indicated in % (w/w). The concentration in the diet of the L2a protease is 100 mg protease enzyme protein per kg of the diet.

TABLE 9

| Diet for layers | |
|---|---|
| Maize | 55.00 |
| Wheat | 10.00 |
| Oat | 7.50 |
| Soya | 20.00 |
| Limestone | 7.50 |
| Premix of Table 8 | 1.00 |

The invention claimed is:

1. A method for improving the nutritional value of an animal feed, comprising adding at least one protease to the feed, wherein the protease has a sequence identity of at least 90% to the sequence of amino acids 1-192 of SEQ ID NO: 2; or is a fragment of the sequence of amino acids 1-192 of SEQ ID NO: 2, that has protease activity.

2. The method of claim 1, wherein the protease has a sequence identity of at least 95% to the sequence of amino acids 1-192 of SEQ ID NO: 2.

3. The method of claim 1, wherein the protease has a degree of sequence identity of at least 97% to the sequence of amino acids 1-192 of SEQ ID NO: 2.

4. The method of claim 1, wherein the protease comprises the sequence of amino acids 1-192 of SEQ ID NO: 2.

5. The method of claim 1, wherein the protease is a fragment of the sequence of amino acids 1-192 of SEQ ID NO: 2.

6. The method of claim 1, further comprising adding amylase; galactanase; alpha-galactosidase; beta-glucanase; phospholipase; phytase; protease, and/or xylanase to the feed.

7. A method for hydrolyzing a protein, comprising adding at least one protease to at least one protein source, wherein the protease has a sequence identity of at least 90% to the sequence of amino acids 1-192 of SEQ ID NO: 2; or is a fragment of the sequence of amino acids 1-192 of SEQ ID NO: 2, that has protease activity, wherein the protein source comprises soybean.

* * * * *

```
                        SEQUENCE LISTING

<160> NUMBER OF SEQ ID NOS: 27

<210> SEQ ID NO 1
<211> LENGTH: 1146
<212> TYPE: DNA
<213> ORGANISM: Nocardiopsis dassonvillei subsp. dassonvillei
<220> FEATURE:
<221> NAME/KEY: CDS
<222> LOCATION: (1)..(1143)
<220> FEATURE:
<221> NAME/KEY: sig_peptide
<222> LOCATION: (1)..(87)
<220> FEATURE:
<221> NAME/KEY: mat_peptide
<222> LOCATION: (568)..(1143)

<400> SEQUENCE: 1 atg cga ccc tcc ccc gct atc tcc gct atc ggc acc ggc gca ctc         45
Met Arg Pro Ser Pro Ala Ile Ser Ala Ile Gly Thr Gly Ala Leu
            -185                -180                -175 gcg ttc ggt ctg gcg ttc tcc gtg acg ccg ggc gcc agt gcg gcg         90
Ala Phe Gly Leu Ala Phe Ser Val Thr Pro Gly Ala Ser Ala Ala
            -170                -165                -160 acc gta ccg gcc gag cca gcg agc gag gcc cag acg atg atg gaa        135
Thr Val Pro Ala Glu Pro Ala Ser Glu Ala Gln Thr Met Met Glu
            -155                -150                -145 gcg ctg cag aga gac ctc ggc ctc acc ccg ctc ggg gcc gag gag        180
Ala Leu Gln Arg Asp Leu Gly Leu Thr Pro Leu Gly Ala Glu Glu
            -140                -135                -130 ctg ctc tcg gcg cag gaa gag gcg atc gag acc gac gcc gag gcc        225
Leu Leu Ser Ala Gln Glu Glu Ala Ile Glu Thr Asp Ala Glu Ala
            -125                -120                -115
```

```
acc gag gcc gcg gga gcg tcc tac ggc ggc tcc ctg ttc gac acc        270
Thr Glu Ala Ala Gly Ala Ser Tyr Gly Gly Ser Leu Phe Asp Thr
            -110            -105             -100 gag acc ctc cag ctc acc gtg ctg gtg acc gac gcc tcg gcc gtg gag    318
Glu Thr Leu Gln Leu Thr Val Leu Val Thr Asp Ala Ser Ala Val Glu
        -95              -90              -85 gcg gtg gag gcc acc ggc gcc gag gcc acc gtg gtc tca cac ggc gca    366
Ala Val Glu Ala Thr Gly Ala Glu Ala Thr Val Val Ser His Gly Ala
            -80              -75              -70 gag ggc ctg gcc gag gtg gtc gac gcg ctc gac gag acc ggc ggc cgg    414
Glu Gly Leu Ala Glu Val Val Asp Ala Leu Asp Glu Thr Gly Gly Arg
        -65              -60              -55 gaa ggg gtc gtc ggc tgg tac ccg gac gtg gag agc gac acc gtc gtg    462
Glu Gly Val Val Gly Trp Tyr Pro Asp Val Glu Ser Asp Thr Val Val
    -50              -45              -40 gtc cag gtc gcc gag ggc gcc agc gcc gac ggc ctc atc gag gcc gcg    510
Val Gln Val Ala Glu Gly Ala Ser Ala Asp Gly Leu Ile Glu Ala Ala
-35              -30              -25              -20 ggc gtg gac ccc tcc gcc gtc cgg gtg gag gag acc agt gag act ccg    558
Gly Val Asp Pro Ser Ala Val Arg Val Glu Glu Thr Ser Glu Thr Pro
            -15              -10               -5 cgc ctg tac gcc gac atc gtc ggc ggc gag gcg tac tac atg ggc ggc    606
Arg Leu Tyr Ala Asp Ile Val Gly Gly Glu Ala Tyr Tyr Met Gly Gly
        -1   1              5                   10 gga cgc tgc tcg gtc ggg ttc gcc gtg acc gac ggc tcc ggc gcg ggc    654
Gly Arg Cys Ser Val Gly Phe Ala Val Thr Asp Gly Ser Gly Ala Gly
    15               20               25 ggc ttc gtg acg gcg ggc cac tgc ggc acc gtc ggc acc ggc gcc gag    702
Gly Phe Val Thr Ala Gly His Cys Gly Thr Val Gly Thr Gly Ala Glu
30               35               40               45 agc tcc gac ggc agc ggc tcc gga acc ttc cag gag tcc gtc ttc ccg    750
Ser Ser Asp Gly Ser Gly Ser Gly Thr Phe Gln Glu Ser Val Phe Pro
            50               55               60 ggc agc gac ggc gcc ttc gtc gcg gcc acc tcc aac tgg aac gtg acc    798
Gly Ser Asp Gly Ala Phe Val Ala Ala Thr Ser Asn Trp Asn Val Thr
        65               70               75 aac ctg gtc agc cgg tac gac tcc ggc agc ccc cag gcg gtg tcg ggt    846
Asn Leu Val Ser Arg Tyr Asp Ser Gly Ser Pro Gln Ala Val Ser Gly
    80               85               90 tcc agc cag gcc ccg gag ggc tcg gcg gtg tgc cgc tcc ggc tcc acc    894
Ser Ser Gln Ala Pro Glu Gly Ser Ala Val Cys Arg Ser Gly Ser Thr
95               100              105 acc ggc tgg cac tgc ggg acc atc gag gcc cgc ggc cag acg gtg aac    942
Thr Gly Trp His Cys Gly Thr Ile Glu Ala Arg Gly Gln Thr Val Asn
110              115              120              125 tac ccg cag ggc acg gtc cag gac ctg acc cgg acg gac gtg tgc gcc    990
Tyr Pro Gln Gly Thr Val Gln Asp Leu Thr Arg Thr Asp Val Cys Ala
            130              135              140 gag ccc ggt gac tcc ggc ggc tcg ttc atc gcc ggt tcg cag gcc cag    1038
Glu Pro Gly Asp Ser Gly Gly Ser Phe Ile Ala Gly Ser Gln Ala Gln
        145              150              155 ggc gtc acc tcc ggc ggc tcg ggc aac tgc acc tcc ggc ggc acg acc    1086
Gly Val Thr Ser Gly Gly Ser Gly Asn Cys Thr Ser Gly Gly Thr Thr
            160              165              170 tac tac cag gag gtc act ccc ctg ctg agc agc tgg ggg ctg tcc ctg    1134
Tyr Tyr Gln Glu Val Thr Pro Leu Leu Ser Ser Trp Gly Leu Ser Leu
175              180              185 gtg acc ggt tag                                                    1146
Val Thr Gly
190
```

<210> SEQ ID NO 2
<211> LENGTH: 381
<212> TYPE: PRT
<213> ORGANISM: Nocardiopsis dassonvillei subsp. dassonvillei

<400> SEQUENCE: 2

```
Met Arg Pro Ser Pro  Ala Ile Ser Ala Ile  Gly Thr Gly Ala Leu
                -185                -180                -175

Ala Phe Gly Leu Ala  Phe Ser Val Thr Pro  Gly Ala Ser Ala Ala
                -170                -165                -160

Thr Val Pro Ala Glu  Pro Ala Ser Glu Ala  Gln Thr Met Met Glu
                -155                -150                -145

Ala Leu Gln Arg Asp  Leu Gly Leu Thr Pro  Leu Gly Ala Glu Glu
                -140                -135                -130

Leu Leu Ser Ala Gln  Glu Glu Ala Ile Glu  Thr Asp Ala Glu Ala
                -125                -120                -115

Thr Glu Ala Ala Gly  Ala Ser Tyr Gly Gly  Ser Leu Phe Asp Thr
                -110                -105                -100

Glu Thr Leu Gln Leu  Thr Val Leu Val Thr  Asp Ala Ser Ala Val Glu
                -95                 -90                 -85

Ala Val Glu Ala Thr  Gly Ala Glu Ala Thr  Val Val Ser His Gly Ala
                -80                 -75                 -70

Glu Gly Leu Ala Glu  Val Val Asp Ala Leu  Asp Glu Thr Gly Gly Arg
            -65                 -60                 -55

Glu Gly Val Val Gly  Trp Tyr Pro Asp Val  Glu Ser Asp Thr Val Val
            -50                 -45                 -40

Val Gln Val Ala Glu  Gly Ala Ser Ala Asp  Gly Leu Ile Glu Ala Ala
-35                  -30                 -25                 -20

Gly Val Asp Pro Ser  Ala Val Arg Val Glu  Glu Thr Ser Glu Thr Pro
                -15                 -10                 -5

Arg Leu Tyr Ala Asp  Ile Val Gly Gly Glu  Ala Tyr Tyr Met Gly Gly
            -1  1                    5                     10

Gly Arg Cys Ser Val  Gly Phe Ala Val Thr  Asp Gly Ser Gly Ala Gly
            15                   20                  25

Gly Phe Val Thr Ala  Gly His Cys Gly Thr  Val Gly Thr Gly Ala Glu
30                   35                  40                  45

Ser Ser Asp Gly Ser  Gly Ser Gly Thr Phe  Gln Glu Ser Val Phe Pro
                50                   55                  60

Gly Ser Asp Gly Ala  Phe Val Ala Ala Thr  Ser Asn Trp Asn Val Thr
            65                   70                  75

Asn Leu Val Ser Arg  Tyr Asp Ser Gly Ser  Pro Gln Ala Val Ser Gly
            80                   85                  90

Ser Ser Gln Ala Pro  Glu Gly Ser Ala Val  Cys Arg Ser Gly Ser Thr
            95                   100                 105

Thr Gly Trp His Cys  Gly Thr Ile Glu Ala  Arg Gly Gln Thr Val Asn
110                  115                 120                 125

Tyr Pro Gln Gly Thr  Val Gln Asp Leu Thr  Arg Thr Asp Val Cys Ala
                130                  135                 140

Glu Pro Gly Asp Ser  Gly Gly Ser Phe Ile  Ala Gly Ser Gln Ala Gln
            145                  150                 155

Gly Val Thr Ser Gly  Gly Ser Gly Asn Cys  Thr Ser Gly Gly Thr Thr
            160                  165                 170

Tyr Tyr Gln Glu Val  Thr Pro Leu Leu Ser  Ser Trp Gly Leu Ser Leu
    175                  180                 185
```

Val Thr Gly
190

<210> SEQ ID NO 3
<211> LENGTH: 1152
<212> TYPE: DNA
<213> ORGANISM: Nocardiopsis prasina DSM 15649
<220> FEATURE:
<221> NAME/KEY: CDS
<222> LOCATION: (1)..(1149)
<220> FEATURE:
<221> NAME/KEY: sig_peptide
<222> LOCATION: (1)..(87)
<220> FEATURE:
<221> NAME/KEY: mat_peptide
<222> LOCATION: (574)..(1149)

<400> SEQUENCE: 3

```
atg cga ccc tcc ccc gtc atc tcc gcg atc ggc acg gga gca ctg         45
Met Arg Pro Ser Pro Val Ile Ser Ala Ile Gly Thr Gly Ala Leu
-190            -185                -180 gcc ttc ggg ctc gcg ctc tcg gtc gcg ccc ggc gcc tcc gcc gtc         90
Ala Phe Gly Leu Ala Leu Ser Val Ala Pro Gly Ala Ser Ala Val
    -175            -170                -165 acc gca ccc acc gag ccc gcg ccc cag ggc gag gcg gcc acc atg        135
Thr Ala Pro Thr Glu Pro Ala Pro Gln Gly Glu Ala Ala Thr Met
-160            -155                -150 cag gaa gcg ctt gag agg gac ttc ggc ctc acc ccg ttc gag gcc        180
Gln Glu Ala Leu Glu Arg Asp Phe Gly Leu Thr Pro Phe Glu Ala
    -145            -140                -135 gaa gac ctg ctc gaa gcc cag aat gac gct ctc ggg atc gac acg        225
Glu Asp Leu Leu Glu Ala Gln Asn Asp Ala Leu Gly Ile Asp Thr
-130            -125                -120 gcg gcg gcc aag gcc gcc ggt gac gcc tac gcg ggc tcc gtg ttc        270
Ala Ala Ala Lys Ala Ala Gly Asp Ala Tyr Ala Gly Ser Val Phe
    -115            -110                -105 gac acc gac acc ctg gaa ctg acc gtc ctg ctc acg gac gcc gga gcc    318
Asp Thr Asp Thr Leu Glu Leu Thr Val Leu Leu Thr Asp Ala Gly Ala
-100                -95                -90 gtg tcg gac gtc gag gcc acc ggc gcc ggg acc gaa ctg gtc tcg tac    366
Val Ser Asp Val Glu Ala Thr Gly Ala Gly Thr Glu Leu Val Ser Tyr
-85             -80                  -75                -70 ggc acc gag ggc ctg gcg gag atc atg gac gag ctc gac gca gcc ggc    414
Gly Thr Glu Gly Leu Ala Glu Ile Met Asp Glu Leu Asp Ala Ala Gly
                -65                  -60                -55 gcc cag ccg ggt gtc gtc ggc tgg tac ccg gac ctc gcc ggc gac acc    462
Ala Gln Pro Gly Val Val Gly Trp Tyr Pro Asp Leu Ala Gly Asp Thr
            -50                  -45                -40 gtc gtc atc gag gcc acc gac acc tcc gag gcc cag agc ttc gtc gag    510
Val Val Ile Glu Ala Thr Asp Thr Ser Glu Ala Gln Ser Phe Val Glu
        -35                  -30                -25 gcc gcg ggc gtg gac tcc tcc gcc gtc cag gtg gag cag acc gac gag    558
Ala Ala Gly Val Asp Ser Ser Ala Val Gln Val Glu Gln Thr Asp Glu
    -20                  -15                -10 gcg ccg cag ctg tac gcc gac atc gtc ggc ggt gac gcc tac tac atg    606
Ala Pro Gln Leu Tyr Ala Asp Ile Val Gly Gly Asp Ala Tyr Tyr Met
-5              -1   1                5                  10 ggc ggc ggg cgc tgc tcg gtc gga ttc gcg gtc acc gac agt tcc ggc    654
Gly Gly Gly Arg Cys Ser Val Gly Phe Ala Val Thr Asp Ser Ser Gly
                15                   20                 25 aac gac gga ttc gtg acg gcc ggc cac tgc ggc acg gtc ggc acc tcc    702
Asn Asp Gly Phe Val Thr Ala Gly His Cys Gly Thr Val Gly Thr Ser
        30                   35                 40
```

-continued

```
gcc agc gag gac ggc agc ggc tcc ggt gtg ttc gag gag tcc atc    750
Ala Asp Ser Glu Asp Gly Ser Gly Ser Gly Val Phe Glu Glu Ser Ile
 45                  50                  55 ttc ccg ggc aac gac gcg gcc ttc gtc agt tcg acg tcc aac tgg acc    798
Phe Pro Gly Asn Asp Ala Ala Phe Val Ser Ser Thr Ser Asn Trp Thr
 60                  65                  70                  75 gtc acc aac ctg gtc aac atg tac agc tcg ggt ggc acc cag tcc gtc    846
Val Thr Asn Leu Val Asn Met Tyr Ser Ser Gly Gly Thr Gln Ser Val
                 80                  85                  90 ggc ggc tcc agc cag gcc ccg gtc ggc gcg gcc gtc tgc cgt tcc ggc    894
Gly Gly Ser Ser Gln Ala Pro Val Gly Ala Ala Val Cys Arg Ser Gly
         95                 100                 105 tcc acc acg ggc tgg cac tgc ggg tcc atc gag gcc cgc ggg cag tcg    942
Ser Thr Thr Gly Trp His Cys Gly Ser Ile Glu Ala Arg Gly Gln Ser
            110                 115                 120 gtg agc tac ccg gag ggc acc gtc acc gac atg acc cgt acc gac gtg    990
Val Ser Tyr Pro Glu Gly Thr Val Thr Asp Met Thr Arg Thr Asp Val
125                 130                 135 tgc gcc gag ccc ggc gac tcc ggc ggt tcg ttc atc gcc gac gac cag   1038
Cys Ala Glu Pro Gly Asp Ser Gly Gly Ser Phe Ile Ala Asp Asp Gln
140                 145                 150                 155 gcc cag ggc atg acc tcg ggc ggc tcc ggc aac tgc tcc tcc ggt ggt   1086
Ala Gln Gly Met Thr Ser Gly Gly Ser Gly Asn Cys Ser Ser Gly Gly
                160                 165                 170 acc acg tac tac cag gag gtc ggc ccg gcg ctg agc acc tgg aac ctc   1134
Thr Thr Tyr Tyr Gln Glu Val Gly Pro Ala Leu Ser Thr Trp Asn Leu
        175                 180                 185 agc ctc gtc acc agc tag                                           1152
Ser Leu Val Thr Ser
            190

<210> SEQ ID NO 4
<211> LENGTH: 383
<212> TYPE: PRT
<213> ORGANISM: Nocardiopsis prasina DSM 15649

<400> SEQUENCE: 4

Met Arg Pro Ser Pro Val Ile Ser Ala Ile Gly Thr Gly Ala Leu
    -190            -185                -180

Ala Phe Gly Leu Ala Leu Ser Val Ala Pro Gly Ala Ser Ala Val
    -175            -170                -165

Thr Ala Pro Thr Glu Pro Ala Pro Gln Gly Glu Ala Ala Thr Met
    -160            -155                -150

Gln Glu Ala Leu Glu Arg Asp Phe Gly Leu Thr Pro Phe Glu Ala
    -145            -140                -135

Glu Asp Leu Leu Glu Ala Gln Asn Asp Ala Leu Gly Ile Asp Thr
    -130            -125                -120

Ala Ala Ala Lys Ala Ala Gly Asp Ala Tyr Ala Gly Ser Val Phe
    -115            -110                -105

Asp Thr Asp Thr Leu Glu Leu Thr Val Leu Leu Thr Asp Ala Gly Ala
    -100             -95                 -90

Val Ser Asp Val Glu Ala Thr Gly Ala Gly Thr Glu Leu Val Ser Tyr
 -85                 -80                 -75                 -70

Gly Thr Glu Gly Leu Ala Glu Ile Met Asp Glu Leu Asp Ala Ala Gly
             -65                 -60                 -55

Ala Gln Pro Gly Val Val Gly Trp Tyr Pro Asp Leu Ala Gly Asp Thr
             -50                 -45                 -40
```

```
Val Val Ile Glu Ala Thr Asp Thr Ser Glu Ala Gln Ser Phe Val Glu
        -35             -30                 -25

Ala Ala Gly Val Asp Ser Ser Ala Val Gln Val Glu Gln Thr Asp Glu
        -20             -15                 -10

Ala Pro Gln Leu Tyr Ala Asp Ile Val Gly Gly Asp Ala Tyr Tyr Met
 -5              -1   1               5                   10

Gly Gly Gly Arg Cys Ser Val Gly Phe Ala Val Thr Asp Ser Ser Gly
             15              20                  25

Asn Asp Gly Phe Val Thr Ala Gly His Cys Gly Thr Val Gly Thr Ser
             30              35              40

Ala Asp Ser Glu Asp Gly Ser Gly Ser Gly Val Phe Glu Glu Ser Ile
 45              50                  55

Phe Pro Gly Asn Asp Ala Ala Phe Val Ser Ser Thr Ser Asn Trp Thr
 60              65              70                  75

Val Thr Asn Leu Val Asn Met Tyr Ser Ser Gly Gly Thr Gln Ser Val
             80                  85                  90

Gly Gly Ser Ser Gln Ala Pro Val Gly Ala Ala Val Cys Arg Ser Gly
             95              100                 105

Ser Thr Thr Gly Trp His Cys Gly Ser Ile Glu Ala Arg Gly Gln Ser
            110              115             120

Val Ser Tyr Pro Glu Gly Thr Val Thr Asp Met Thr Arg Thr Asp Val
            125              130             135

Cys Ala Glu Pro Gly Asp Ser Gly Gly Ser Phe Ile Ala Asp Asp Gln
140              145             150                 155

Ala Gln Gly Met Thr Ser Gly Ser Gly Asn Cys Ser Ser Gly Gly
             160             165                 170

Thr Thr Tyr Tyr Gln Glu Val Gly Pro Ala Leu Ser Thr Trp Asn Leu
            175              180             185

Ser Leu Val Thr Ser
            190

<210> SEQ ID NO 5
<211> LENGTH: 1152
<212> TYPE: DNA
<213> ORGANISM: Nocardiopsis prasina DSM 14010
<220> FEATURE:
<221> NAME/KEY: CDS
<222> LOCATION: (1)..(1149)
<220> FEATURE:
<221> NAME/KEY: sig_peptide
<222> LOCATION: (1)..(87)
<220> FEATURE:
<221> NAME/KEY: mat_peptide
<222> LOCATION: (574)..(1149)

<400> SEQUENCE: 5 atg cga ccc tcc ccc gtc atc tcc gcg atc ggc acg gga gcg ctg      45
Met Arg Pro Ser Pro Val Ile Ser Ala Ile Gly Thr Gly Ala Leu
    -190            -185                -180 gcc ttc ggg ctc gcg ctc tcg gtc gct ccc ggc gcc tcc gcc gtg      90
Ala Phe Gly Leu Ala Leu Ser Val Ala Pro Gly Ala Ser Ala Val
    -175            -170                -165 acc gcc ccc gcc gag ccc tcg ccc cag ggc gag gcg acc acc atg     135
Thr Ala Pro Ala Glu Pro Ser Pro Gln Gly Glu Ala Thr Thr Met
    -160            -155                -150 cag gaa gcg ctt gag agg gac ttc ggc ctc acc ccg ttc gag gcc     180
Gln Glu Ala Leu Glu Arg Asp Phe Gly Leu Thr Pro Phe Glu Ala
    -145            -140                -135 gac gac ctg ctc gaa gcc cag aag gag gcc ctc ggg atc gac acg     225
Asp Asp Leu Leu Glu Ala Gln Lys Glu Ala Leu Gly Ile Asp Thr
```

```
                          -continued

Asp Asp  Leu Leu Glu Ala Gln  Lys Glu Ala Leu Gly  Ile Asp Thr
    -130             -125                 -120 gcg gcg gcc gag gcc gcc ggc gac gcc tac gcg ggc tcc gtg ttc        270
Ala Ala Ala Glu Ala Ala Gly Asp Ala Tyr Ala Gly Ser Val Phe
    -115             -110             -105 gac acc gac acc ctg gaa ctg acc gtc ctg ctc acg gac ggc ggc ccg    318
Asp Thr Asp Thr Leu Glu Leu Thr Val Leu Leu Thr Asp Gly Gly Pro
    -100                -95                  -90 gcg tcg gac gtc gag gcc gcc ggc gcc gag acc tcg gtg gtc tcc cac    366
Ala Ser Asp Val Glu Ala Ala Gly Ala Glu Thr Ser Val Val Ser His
-85                 -80                  -75                 -70 ggc acc gac ggc ctg gcg gcg atc atg gac gag ctc gac gcg gtc ggc    414
Gly Thr Asp Gly Leu Ala Ala Ile Met Asp Glu Leu Asp Ala Val Gly
                -65                  -60                 -55 gcc cag ccg ggt gtc gtc ggc tgg tac ccc gac ctc gcc agc gac acg    462
Ala Gln Pro Gly Val Val Gly Trp Tyr Pro Asp Leu Ala Ser Asp Thr
            -50                  -45                 -40 gtg gtc gtc gag gcc acc gac gcg tcc gac gcc cag ggc ttc atc gag    510
Val Val Val Glu Ala Thr Asp Ala Ser Asp Ala Gln Gly Phe Ile Glu
        -35                  -30                 -25 gcc gcc ggc gtg gac tcc tcc gcc gtc cag gtg gag gag acc gac gag    558
Ala Ala Gly Val Asp Ser Ser Ala Val Gln Val Glu Glu Thr Asp Glu
    -20                  -15                 -10 tcg ccc gag ctg tac gcc gac atc gtc ggc ggc gac gcc tac tac atg    606
Ser Pro Glu Leu Tyr Ala Asp Ile Val Gly Gly Asp Ala Tyr Tyr Met
-5              -1  1                5                  10 ggc ggc gga cgc tgc tcg gtg ggc ttc gcg gcc acc gac agc gcg ggc    654
Gly Gly Gly Arg Cys Ser Val Gly Phe Ala Ala Thr Asp Ser Ala Gly
                15                  20                  25 aac gac gga ttc gtg acg gcc ggc cac tgc ggc acc gtc ggc acc tcc    702
Asn Asp Gly Phe Val Thr Ala Gly His Cys Gly Thr Val Gly Thr Ser
            30                  35                  40 gcc gac agc gag gac ggc agc ggc tcc ggt gtg ttc gag gag tcg atc    750
Ala Asp Ser Glu Asp Gly Ser Gly Ser Gly Val Phe Glu Glu Ser Ile
45                  50                  55 ttc ccg ggc aac gac gcc gcc ttc gtc cgg tcc acg tcc aac tgg acc    798
Phe Pro Gly Asn Asp Ala Ala Phe Val Arg Ser Thr Ser Asn Trp Thr
60                  65                  70                  75 gtc acc aac ctg gtc aac atg tac agc tcc ggc ggc acc cag tcc gtc    846
Val Thr Asn Leu Val Asn Met Tyr Ser Ser Gly Gly Thr Gln Ser Val
                80                  85                  90 ggc ggc tcc acc cag gcc ccg gtc ggc gcg gcc gtg tgc cgc tcc ggt    894
Gly Gly Ser Thr Gln Ala Pro Val Gly Ala Ala Val Cys Arg Ser Gly
            95                  100                 105 tcc acc acg ggc tgg cac tgc ggc acc atc gag gcc cga ggc cag tcg    942
Ser Thr Thr Gly Trp His Cys Gly Thr Ile Glu Ala Arg Gly Gln Ser
        110                 115                 120 gtg agc tac ccg gag ggc acc gtc aac gac atg acc cgg acc aac gtg    990
Val Ser Tyr Pro Glu Gly Thr Val Asn Asp Met Thr Arg Thr Asn Val
    125                 130                 135 tgc gcc gag ccc ggc gac tcc ggc ggt tcg ttc atc tcc gac gac cag   1038
Cys Ala Glu Pro Gly Asp Ser Gly Gly Ser Phe Ile Ser Asp Asp Gln
140                 145                 150                 155 gcc cag ggc atg acc tcg ggc ggc tcc ggc aac tgc acc tcc ggt ggt   1086
Ala Gln Gly Met Thr Ser Gly Gly Ser Gly Asn Cys Thr Ser Gly Gly
                160                 165                 170 acg acg tac tac cag gag gtc ggc ccg gcg ctg agc acc tgg aac ctc   1134
Thr Thr Tyr Tyr Gln Glu Val Gly Pro Ala Leu Ser Thr Trp Asn Leu
            175                 180                 185
```

```
agc ctc gtc acg agc tag                                    1152
Ser Leu Val Thr Ser
        190

<210> SEQ ID NO 6
<211> LENGTH: 383
<212> TYPE: PRT
<213> ORGANISM: Nocardiopsis prasina DSM 14010

<400> SEQUENCE: 6

Met Arg  Pro Ser Pro Val Ile  Ser Ala Ile Gly Thr  Gly Ala Leu
        -190             -185              -180

Ala Phe  Gly Leu Ala Leu Ser  Val Ala Pro Gly Ala  Ser Ala Val
        -175             -170              -165

Thr Ala  Pro Ala Glu Pro Ser  Pro Gln Gly Glu Ala  Thr Thr Met
        -160             -155              -150

Gln Glu  Ala Leu Glu Arg Asp  Phe Gly Leu Thr Pro  Phe Glu Ala
        -145             -140              -135

Asp Asp  Leu Leu Glu Ala Gln  Lys Glu Ala Leu Gly  Ile Asp Thr
        -130             -125              -120

Ala Ala  Ala Glu Ala Ala Gly  Asp Ala Tyr Ala Gly  Ser Val Phe
        -115             -110              -105

Asp Thr  Asp Thr Leu Glu Leu  Thr Val Leu Leu Thr  Asp Gly Gly Pro
        -100              -95              -90

Ala Ser  Asp Val Glu Ala Ala  Gly Ala Glu Thr Ser  Val Val Ser His
 -85              -80              -75               -70

Gly Thr  Asp Gly Leu Ala Ala  Ile Met Asp Glu Leu  Asp Ala Val Gly
                 -65              -60               -55

Ala Gln  Pro Gly Val Val Gly  Trp Tyr Pro Asp Leu  Ala Ser Asp Thr
                 -50              -45               -40

Val Val  Val Glu Ala Thr Asp  Ala Ser Asp Ala Gln  Gly Phe Ile Glu
                 -35              -30               -25

Ala Ala  Gly Val Asp Ser Ser  Ala Val Gln Val Glu  Glu Thr Asp Glu
                 -20              -15               -10

Ser Pro  Glu Leu Tyr Ala Asp  Ile Val Gly Gly Asp  Ala Tyr Tyr Met
 -5               -1   1                5                      10

Gly Gly  Gly Arg Cys Ser Val  Gly Phe Ala Ala Thr  Asp Ser Ala Gly
                  15               20                     25

Asn Asp  Gly Phe Val Thr Ala  Gly His Cys Gly Thr  Val Gly Thr Ser
                  30               35                     40

Ala Asp  Ser Glu Asp Gly Ser  Gly Ser Gly Val Phe  Glu Glu Ser Ile
         45                    50                         55

Phe Pro  Gly Asn Asp Ala Ala  Phe Val Arg Ser Thr  Ser Asn Trp Thr
 60               65                    70                     75

Val Thr  Asn Leu Val Asn Met  Tyr Ser Ser Gly Thr  Gln Ser Val
                  80               85                     90

Gly Gly  Ser Thr Gln Ala Pro  Val Gly Ala Ala Val  Cys Arg Ser Gly
                  95              100                    105

Ser Thr  Thr Gly Trp His Cys  Gly Thr Ile Glu Ala  Arg Gly Gln Ser
                 110              115                    120

Val Ser  Tyr Pro Glu Gly Thr  Val Asn Asp Met Thr  Arg Thr Asn Val
                 125              130                    135

Cys Ala  Glu Pro Gly Asp Ser  Gly Gly Ser Phe Ile  Ser Asp Asp Gln
 140              145                   150                    155

Ala Gln  Gly Met Thr Ser Gly  Gly Ser Gly Asn Cys  Thr Ser Gly Gly
```

```
                     160                 165                 170
Thr Thr Tyr Tyr Gln Glu Val Gly Pro Ala Leu Ser Thr Trp Asn Leu
        175                 180                 185

Ser Leu Val Thr Ser
        190

<210> SEQ ID NO 7
<211> LENGTH: 1155
<212> TYPE: DNA
<213> ORGANISM: Nocardiopsis sp. DSM 16424
<220> FEATURE:
<221> NAME/KEY: CDS
<222> LOCATION: (1)..(1152)
<220> FEATURE:
<221> NAME/KEY: sig_peptide
<222> LOCATION: (1)..(87)
<220> FEATURE:
<221> NAME/KEY: mat_peptide
<222> LOCATION: (586)..(1152)

<400> SEQUENCE: 7 atg aga ccc tcc acc atc gcc tcc gcc gtc ggc aca gga gca ctg        45
Met Arg Pro Ser Thr Ile Ala Ser Ala Val Gly Thr Gly Ala Leu
-195                -190                -185 gcc ttc ggt ctg gca ctg tcc atg gcc ccc gga gcc ctc gcg gcg        90
Ala Phe Gly Leu Ala Leu Ser Met Ala Pro Gly Ala Leu Ala Ala
        -180                -175                -170 ccc ggc ccc gtc ccc cag acc ccc gtc gcc gac gac agc gcc gcc       135
Pro Gly Pro Val Pro Gln Thr Pro Val Ala Asp Asp Ser Ala Ala
-165                -160                -155 agc atg acc gaa gcg ctc aag cgt gac ctc aac ctc tcc tcg gcc       180
Ser Met Thr Glu Ala Leu Lys Arg Asp Leu Asn Leu Ser Ser Ala
-150                -145                -140 gag gcc gag gag ctg ctc tcg gcg cag gaa gcc gcg atc gag acc       225
Glu Ala Glu Glu Leu Leu Ser Ala Gln Glu Ala Ala Ile Glu Thr
-135                -130                -125 gac gcc gag gcc gcc gag gcc gcg gga gag gcc tac ggc ggc tcc       270
Asp Ala Glu Ala Ala Glu Ala Ala Gly Glu Ala Tyr Gly Gly Ser
-120                -115                -110 ctg ttc gac acc gaa acc ctc gaa ctc acc gtg ctg gtg acc gac acc   318
Leu Phe Asp Thr Glu Thr Leu Glu Leu Thr Val Leu Val Thr Asp Thr
-105                -100                -95                 -90 acg gcc gtc gac gcg gtc gag gcc acc gga gcc gag gcc acc gtg gtc   366
Thr Ala Val Asp Ala Val Glu Ala Thr Gly Ala Glu Ala Thr Val Val
                -85                 -80                 -75 acc cac ggc acc gac ggc ctg gcc gag gtc gtg gag gac ctc aac agc   414
Thr His Gly Thr Asp Gly Leu Ala Glu Val Val Glu Asp Leu Asn Ser
        -70                 -65                 -60 gcc gac gcc ccg gcg ggc gtc ctc ggc tgg tac ccc gac atg gag agc   462
Ala Asp Ala Pro Ala Gly Val Leu Gly Trp Tyr Pro Asp Met Glu Ser
        -55                 -50                 -45 gac acc gtg gtg gtc gag gtg ctg gag ggc tcc gac gcc gac gtc gcc   510
Asp Thr Val Val Val Glu Val Leu Glu Gly Ser Asp Ala Asp Val Ala
        -40                 -35                 -30 gcc ctg ctc gcc gac gcc ggc gtg gac gcc tcc gcc gtc cgg gtg gag   558
Ala Leu Leu Ala Asp Ala Gly Val Asp Ala Ser Ala Val Arg Val Glu
-25                 -20                 -15                 -10 gag gcg gag gag gtc ccg cag gtc tac gcc aac atc atc ggc ggc ctg   606
Glu Ala Glu Glu Val Pro Gln Val Tyr Ala Asn Ile Ile Gly Gly Leu
                -5                  -1 1                 5 gcc tac acc atg ggc gga cgc tgc tcc gtc ggc ttc gcg gcg acc aac   654
Ala Tyr Thr Met Gly Gly Arg Cys Ser Val Gly Phe Ala Ala Thr Asn
```

```
            10                  15                  20
agc gcc gga cag ccc ggt ttc gtg acg gcg ggc cac tgc ggc acc gtc       702
Ser Ala Gly Gln Pro Gly Phe Val Thr Ala Gly His Cys Gly Thr Val
    25                  30                  35 ggc acc gcc gtg acc atc ggc gac ggc cgc ggc gtc ttc gag cgc tcg       750
Gly Thr Ala Val Thr Ile Gly Asp Gly Arg Gly Val Phe Glu Arg Ser
40                  45                  50                  55 gtc ttc ccc ggc aac gac gcc gcc ttc gtc cgc ggc acc tcc aac ttc       798
Val Phe Pro Gly Asn Asp Ala Ala Phe Val Arg Gly Thr Ser Asn Phe
                60                  65                  70 acc ctg acc aac ctg gtc tcc cgc tac aac tcc ggc ggc cac cag gcg       846
Thr Leu Thr Asn Leu Val Ser Arg Tyr Asn Ser Gly Gly His Gln Ala
        75                  80                  85 gtg acc ggc acc agc cag gcc ccg gcc ggc tcg gcc gtc tgc cgc tcc       894
Val Thr Gly Thr Ser Gln Ala Pro Ala Gly Ser Ala Val Cys Arg Ser
    90                  95                  100 ggc tcc acc acc ggc tgg cac tgc ggc acc atc cag gcc cgc aac cag       942
Gly Ser Thr Thr Gly Trp His Cys Gly Thr Ile Gln Ala Arg Asn Gln
105                 110                 115 acc gtg cgc tac ccg cag ggc acc gtc aac gcg ctc acc cgc acc aac       990
Thr Val Arg Tyr Pro Gln Gly Thr Val Asn Ala Leu Thr Arg Thr Asn
120                 125                 130                 135 gtg tgc gcc gag ccc ggt gac tcc ggc ggc tcg ttc atc tcc ggc tcg      1038
Val Cys Ala Glu Pro Gly Asp Ser Gly Gly Ser Phe Ile Ser Gly Ser
                140                 145                 150 cag gcc cag ggc gtc acc tcc ggc ggc tcc ggc aac tgc tcc ttc ggc      1086
Gln Ala Gln Gly Val Thr Ser Gly Gly Ser Gly Asn Cys Ser Phe Gly
        155                 160                 165 ggc acg acc tac tac cag gag gtc gcc ccg atg atc aac tcc tgg ggc      1134
Gly Thr Thr Tyr Tyr Gln Glu Val Ala Pro Met Ile Asn Ser Trp Gly
    170                 175                 180 gtt cgc atc cgc acc agc tga                                          1155
Val Arg Ile Arg Thr Ser
        185

<210> SEQ ID NO 8
<211> LENGTH: 384
<212> TYPE: PRT
<213> ORGANISM: Nocardiopsis sp. DSM 16424

<400> SEQUENCE: 8

Met  Arg  Pro  Ser  Thr  Ile  Ala  Ser  Ala  Val  Gly  Thr  Gly  Ala  Leu
-195            -190                -185

Ala  Phe  Gly  Leu  Ala  Leu  Ser  Met  Ala  Pro  Gly  Ala  Leu  Ala  Ala
-180            -175                -170

Pro  Gly  Pro  Val  Pro  Gln  Thr  Pro  Val  Ala  Asp  Asp  Ser  Ala  Ala
-165            -160                -155

Ser  Met  Thr  Glu  Ala  Leu  Lys  Arg  Asp  Leu  Asn  Leu  Ser  Ser  Ala
-150            -145                -140

Glu  Ala  Glu  Glu  Leu  Leu  Ser  Ala  Gln  Glu  Ala  Ala  Ile  Glu  Thr
-135            -130                -125

Asp  Ala  Glu  Ala  Ala  Glu  Ala  Ala  Gly  Glu  Ala  Tyr  Gly  Gly  Ser
-120            -115                -110

Leu  Phe  Asp  Thr  Glu  Thr  Leu  Glu  Leu  Thr  Val  Leu  Val  Thr  Asp
-105            -100                -95                 -90

Thr  Ala  Val  Asp  Ala  Val  Glu  Ala  Thr  Gly  Ala  Glu  Ala  Thr  Val  Val
                -85                 -80                 -75

Thr  His  Gly  Thr  Asp  Gly  Leu  Ala  Glu  Val  Val  Glu  Asp  Leu  Asn  Ser
```

```
                   -70            -65              -60
Ala Asp Ala Pro Ala Gly Val Leu Gly Trp Tyr Pro Asp Met Glu Ser
            -55                -50              -45

Asp Thr Val Val Glu Val Leu Glu Gly Ser Asp Ala Asp Val Ala
        -40                -35              -30

Ala Leu Leu Ala Asp Ala Gly Val Asp Ala Ser Ala Val Arg Val Glu
-25                -20              -15                  -10

Glu Ala Glu Glu Val Pro Gln Val Tyr Ala Asn Ile Ile Gly Gly Leu
                -5              -1   1                5

Ala Tyr Thr Met Gly Gly Arg Cys Ser Val Gly Phe Ala Ala Thr Asn
            10              15                  20

Ser Ala Gly Gln Pro Gly Phe Val Thr Ala Gly His Cys Gly Thr Val
        25                30                35

Gly Thr Ala Val Thr Ile Gly Asp Gly Arg Gly Val Phe Glu Arg Ser
40              45                50                  55

Val Phe Pro Gly Asn Asp Ala Ala Phe Val Arg Gly Thr Ser Asn Phe
                60              65                  70

Thr Leu Thr Asn Leu Val Ser Arg Tyr Asn Ser Gly Gly His Gln Ala
            75              80              85

Val Thr Gly Thr Ser Gln Ala Pro Ala Gly Ser Ala Val Cys Arg Ser
        90              95                  100

Gly Ser Thr Thr Gly Trp His Cys Gly Thr Ile Gln Ala Arg Asn Gln
105              110                115

Thr Val Arg Tyr Pro Gln Gly Thr Val Asn Ala Leu Thr Arg Thr Asn
120              125              130                  135

Val Cys Ala Glu Pro Gly Asp Ser Gly Gly Ser Phe Ile Ser Gly Ser
            140              145                  150

Gln Ala Gln Gly Val Thr Ser Gly Gly Ser Gly Asn Cys Ser Phe Gly
            155              160              165

Gly Thr Thr Tyr Tyr Gln Glu Val Ala Pro Met Ile Asn Ser Trp Gly
            170              175              180

Val Arg Ile Arg Thr Ser
    185
```

<210> SEQ ID NO 9
<211> LENGTH: 1152
<212> TYPE: DNA
<213> ORGANISM: Nocardiopsis alkaliphila DSM 44657
<220> FEATURE:
<221> NAME/KEY: CDS
<222> LOCATION: (1)..(1149)
<220> FEATURE:
<221> NAME/KEY: sig_peptide
<222> LOCATION: (1)..(87)
<220> FEATURE:
<221> NAME/KEY: mat_peptide
<222> LOCATION: (586)..(1149)

<400> SEQUENCE: 9

```
atg cga ccc tcc ccc gtt gtc tcc gcc ata ggt aca gga gcc ttg       45
Met Arg Pro Ser Pro Val Val Ser Ala Ile Gly Thr Gly Ala Leu
-195              -190              -185 gcc ttc ggc ctg gct ctg ggc act tcc ccc gcg gcc atc gcc gcc       90
Ala Phe Gly Leu Ala Leu Gly Thr Ser Pro Ala Ala Ile Ala Ala
-180              -175              -170 ccc gcc ccc cag tcc ccc gac acc gaa acg cag gcc gag gcc gtc      135
Pro Ala Pro Gln Ser Pro Asp Thr Glu Thr Gln Ala Glu Ala Val
-165              -160              -155
```

-continued

```
acc atg gcc gaa gcc ctc caa cgc gat ctc ggt ctg tcc tcc tcc       180
Thr Met Ala Glu Ala Leu Gln Arg Asp Leu Gly Leu Ser Ser Ser
-150         -145                 -140 gag gcc acc gaa ctc ctc gcc gca cag gcc gag gcg ttc gag gtc       225
Glu Ala Thr Glu Leu Leu Ala Ala Gln Ala Glu Ala Phe Glu Val
-135         -130                 -125 gac gag gcc gcc acc gag gcc gcc gcc gac gcc tac ggc ggc tcc       270
Asp Glu Ala Ala Thr Glu Ala Ala Ala Asp Ala Tyr Gly Gly Ser
-120         -115                 -110 ctc ttc gac acc gac agc ctc gaa ctg acc gtg ctg gtc acc gac agc   318
Leu Phe Asp Thr Asp Ser Leu Glu Leu Thr Val Leu Val Thr Asp Ser
-105         -100                 -95                  -90 gcc gcc gtc gac gcg gtc gag gcc acc ggc gcc aag gcc gag gtc gtc   366
Ala Ala Val Asp Ala Val Glu Ala Thr Gly Ala Lys Ala Glu Val Val
             -85                  -80                  -75 gac cac ggt atc gag ggc ctc gag gag atc gtc gac gaa ctc aac gag   414
Asp His Gly Ile Glu Gly Leu Glu Glu Ile Val Asp Glu Leu Asn Glu
                 -70                  -65                  -60 tcc aac gcc aag tcg ggc gtc gtc ggt tgg tac ccc gac gtg gcc ggt   462
Ser Asn Ala Lys Ser Gly Val Val Gly Trp Tyr Pro Asp Val Ala Gly
         -55                  -50                  -45 gac acg gtc gtc ctg gag gtc atg gaa ggc tcc gag gcc gac gtg gac   510
Asp Thr Val Val Leu Glu Val Met Glu Gly Ser Glu Ala Asp Val Asp
     -40                  -35                  -30 gcc ctg ctc gcc gag acc ggg gtc gac gcc gcc gac gtc acg gtg gag   558
Ala Leu Leu Ala Glu Thr Gly Val Asp Ala Ala Asp Val Thr Val Glu
-25                  -20                  -15                  -10 acc acc acc gag cag ccc gag ctc tac gcc gac atc atc ggt ggc ctg   606
Thr Thr Thr Glu Gln Pro Glu Leu Tyr Ala Asp Ile Ile Gly Gly Leu
                 -5                   -1  1                5 gcc tac acc atg ggc gga cgt tgc tcg gtc ggc ttc gcc gcc acc aac   654
Ala Tyr Thr Met Gly Gly Arg Cys Ser Val Gly Phe Ala Ala Thr Asn
         10                  15                  20 tcc tcc ggc cag ccc gga ttc gtc acc gcc ggc cac tgc ggc agt gtc   702
Ser Ser Gly Gln Pro Gly Phe Val Thr Ala Gly His Cys Gly Ser Val
     25                  30                  35 ggc acc ggc gtc acc atc ggt aac ggc cgg ggc gtc ttc gag cgt tcc   750
Gly Thr Gly Val Thr Ile Gly Asn Gly Arg Gly Val Phe Glu Arg Ser
40                   45                  50                  55 atc ttc ccg ggc aac gac gcc gcc ttc gtc cgt ggc acg tcc aac ttc   798
Ile Phe Pro Gly Asn Asp Ala Ala Phe Val Arg Gly Thr Ser Asn Phe
                 60                  65                  70 acc ctg acc aac ctg gtc agc cgc tac aac tcc ggc ggc tac gcc acg   846
Thr Leu Thr Asn Leu Val Ser Arg Tyr Asn Ser Gly Gly Tyr Ala Thr
         75                  80                  85 gtg tcc ggg tcc tcc gcg gcc ccg atc ggc tcc cag gtg tgc cgc tcc   894
Val Ser Gly Ser Ser Ala Ala Pro Ile Gly Ser Gln Val Cys Arg Ser
     90                  95                  100 ggc tcc acc acc ggc tgg cac tgc ggc acc atc cag gcc cgc aac cag   942
Gly Ser Thr Thr Gly Trp His Cys Gly Thr Ile Gln Ala Arg Asn Gln
105                  110                 115 acg gtg cgc tac ccg cag ggc acc gtc cag gcc ctg acc cgc acc agc   990
Thr Val Arg Tyr Pro Gln Gly Thr Val Gln Ala Leu Thr Arg Thr Ser
120                  125                 130                 135 gtg tgc gcc gag ccc ggt gac tcc ggt ggt tcc ttc atc tcc ggc agc   1038
Val Cys Ala Glu Pro Gly Asp Ser Gly Gly Ser Phe Ile Ser Gly Ser
                 140                 145                 150 cag gcc cag ggc gtc acc tcc ggt ggc tcg ggc aac tgc cgc acc ggt   1086
Gln Ala Gln Gly Val Thr Ser Gly Gly Ser Gly Asn Cys Arg Thr Gly
         155                 160                 165
```

```
ggc acg acc tac tac cag gag gtc aac ccc atg ctc aac agc tgg ggc      1134
Gly Thr Thr Tyr Tyr Gln Glu Val Asn Pro Met Leu Asn Ser Trp Gly
        170                 175                 180 ctg cgt ctg cgc acc tga                                              1152
Leu Arg Leu Arg Thr
    185

<210> SEQ ID NO 10
<211> LENGTH: 383
<212> TYPE: PRT
<213> ORGANISM: Nocardiopsis alkaliphila DSM 44657

<400> SEQUENCE: 10

Met  Arg  Pro  Ser  Pro  Val  Val  Ser  Ala  Ile  Gly  Thr  Gly  Ala  Leu
-195                -190                -185

Ala  Phe  Gly  Leu  Ala  Leu  Gly  Thr  Ser  Pro  Ala  Ala  Ile  Ala  Ala
-180                -175                -170

Pro  Ala  Pro  Gln  Ser  Pro  Asp  Thr  Glu  Thr  Gln  Ala  Glu  Ala  Val
-165                -160                -155

Thr  Met  Ala  Glu  Ala  Leu  Gln  Arg  Asp  Leu  Gly  Leu  Ser  Ser  Ser
-150                -145                -140

Glu  Ala  Thr  Glu  Leu  Leu  Ala  Ala  Gln  Ala  Glu  Ala  Phe  Glu  Val
-135                -130                -125

Asp  Glu  Ala  Ala  Thr  Glu  Ala  Ala  Ala  Asp  Ala  Tyr  Gly  Gly  Ser
-120                -115                -110

Leu  Phe  Asp  Thr  Asp  Ser  Leu  Glu  Leu  Thr  Val  Leu  Val  Thr  Asp  Ser
-105                -100                 -95                              -90

Ala  Ala  Val  Asp  Ala  Val  Glu  Ala  Thr  Gly  Ala  Lys  Ala  Glu  Val  Val
                 -85                 -80                 -75

Asp  His  Gly  Ile  Glu  Gly  Leu  Glu  Glu  Ile  Val  Asp  Glu  Leu  Asn  Glu
             -70                 -65                 -60

Ser  Asn  Ala  Lys  Ser  Gly  Val  Val  Gly  Trp  Tyr  Pro  Asp  Val  Ala  Gly
         -55                 -50                 -45

Asp  Thr  Val  Val  Leu  Glu  Val  Met  Glu  Gly  Ser  Glu  Ala  Asp  Val  Asp
     -40                 -35                 -30

Ala  Leu  Leu  Ala  Glu  Thr  Gly  Val  Asp  Ala  Ala  Asp  Val  Thr  Val  Glu
-25                 -20                 -15                 -10

Thr  Thr  Thr  Glu  Gln  Pro  Glu  Leu  Tyr  Ala  Asp  Ile  Ile  Gly  Gly  Leu
                 -5                 -1  1                  5

Ala  Tyr  Thr  Met  Gly  Gly  Arg  Cys  Ser  Val  Gly  Phe  Ala  Ala  Thr  Asn
             10                  15                  20

Ser  Ser  Gly  Gln  Pro  Gly  Phe  Val  Thr  Ala  Gly  His  Cys  Gly  Ser  Val
         25                  30                  35

Gly  Thr  Gly  Val  Thr  Ile  Gly  Asn  Gly  Arg  Gly  Val  Phe  Glu  Arg  Ser
40                  45                  50                  55

Ile  Phe  Pro  Gly  Asn  Asp  Ala  Ala  Phe  Val  Arg  Gly  Thr  Ser  Asn  Phe
             60                  65                  70

Thr  Leu  Thr  Asn  Leu  Val  Ser  Arg  Tyr  Asn  Ser  Gly  Gly  Tyr  Ala  Thr
         75                  80                  85

Val  Ser  Gly  Ser  Ser  Ala  Ala  Pro  Ile  Gly  Ser  Gln  Val  Cys  Arg  Ser
     90                  95                 100

Gly  Ser  Thr  Thr  Gly  Trp  His  Cys  Gly  Thr  Ile  Gln  Ala  Arg  Asn  Gln
     105                 110                 115

Thr  Val  Arg  Tyr  Pro  Gln  Gly  Thr  Val  Gln  Ala  Leu  Thr  Arg  Thr  Ser
120                 125                 130                 135
```

```
Val Cys Ala Glu Pro Gly Asp Ser Gly Gly Ser Phe Ile Ser Gly Ser
            140                 145                 150

Gln Ala Gln Gly Val Thr Ser Gly Gly Ser Gly Asn Cys Arg Thr Gly
        155                 160                 165

Gly Thr Thr Tyr Tyr Gln Glu Val Asn Pro Met Leu Asn Ser Trp Gly
    170                 175                 180

Leu Arg Leu Arg Thr
    185

<210> SEQ ID NO 11
<211> LENGTH: 1155
<212> TYPE: DNA
<213> ORGANISM: Nocardiopsis lucentensis DSM 44048
<220> FEATURE:
<221> NAME/KEY: CDS
<222> LOCATION: (1)..(1152)
<220> FEATURE:
<221> NAME/KEY: sig_peptide
<222> LOCATION: (1)..(87)
<220> FEATURE:
<221> NAME/KEY: mat_peptide
<222> LOCATION: (586)..(1152)

<400> SEQUENCE: 11
```

| | | | | | | | | | | | | | | | |
|---|---|---|---|---|---|---|---|---|---|---|---|---|---|---|---|
| atg | cga | ccc | tcc | ccc | gtt | atc | tcc | gcc | cta | gga | acc | ggc | gcc | ctc | 45 |
| Met | Arg | Pro | Ser | Pro | Val | Ile | Ser | Ala | Leu | Gly | Thr | Gly | Ala | Leu | |
| -195 | | | | -190 | | | | | -185 | | | | | | |
| gcc | ttc | gga | ctg | gtc | atc | acc | atg | gcc | ccg | ggc | gtg | aac | gcc | gga | 90 |
| Ala | Phe | Gly | Leu | Val | Ile | Thr | Met | Ala | Pro | Gly | Val | Asn | Ala | Gly | |
| -180 | | | | | -175 | | | | | -170 | | | | | |
| acc | gta | ccc | acc | ccc | cag | gcc | ccc | gtc | ccc | gac | gac | gag | gcc | acc | 135 |
| Thr | Val | Pro | Thr | Pro | Gln | Ala | Pro | Val | Pro | Asp | Asp | Glu | Ala | Thr | |
| -165 | | | | | -160 | | | | | -155 | | | | | |
| acc | atg | ctc | gaa | gcc | atg | gag | agg | gat | ctc | gac | ctc | acc | ccg | ttc | 180 |
| Thr | Met | Leu | Glu | Ala | Met | Glu | Arg | Asp | Leu | Asp | Leu | Thr | Pro | Phe | |
| -150 | | | | | -145 | | | | | -140 | | | | | |
| gag | gcc | gag | gaa | ctc | ttc | gag | gca | cag | gaa | gag | gcc | atc | gac | ctc | 225 |
| Glu | Ala | Glu | Glu | Leu | Phe | Glu | Ala | Gln | Glu | Glu | Ala | Ile | Asp | Leu | |
| -135 | | | | | -130 | | | | | -125 | | | | | |
| gac | gag | gag | gcc | acc | gaa | gcg | gcc | ggt | gcg | gcc | tac | ggc | ggt | tcg | 270 |
| Asp | Glu | Glu | Ala | Thr | Glu | Ala | Ala | Gly | Ala | Ala | Tyr | Gly | Gly | Ser | |
| -120 | | | | | -115 | | | | | -110 | | | | | |
| ctc | ttc | gac | acc | gaa | acc | cac | gaa | ctc | acc | gtc | ctg | gtg | acc | gac | gtc | 318 |
| Leu | Phe | Asp | Thr | Glu | Thr | His | Glu | Leu | Thr | Val | Leu | Val | Thr | Asp | Val |
| -105 | | | | | -100 | | | | | -95 | | | | -90 | | |
| gac | gcg | gtc | gag | gcc | gtg | gag | gcc | acc | gga | gcc | gcc | gcc | gag | gtc | gtc | 366 |
| Asp | Ala | Val | Glu | Ala | Val | Glu | Ala | Thr | Gly | Ala | Ala | Ala | Glu | Val | Val |
| | | | -85 | | | | | -80 | | | | | -75 | | |
| tcc | cac | ggc | tcc | gac | ggt | ctg | gcc | gac | atc | gtc | gag | gac | ctc | aac | gcc | 414 |
| Ser | His | Gly | Ser | Asp | Gly | Leu | Ala | Asp | Ile | Val | Glu | Asp | Leu | Asn | Ala |
| | | | -70 | | | | | -65 | | | | | -60 | | |
| acc | gac | gcc | ggc | agc | gag | gtc | gtg | ggc | tgg | tac | ccc | gac | gtc | acc | agc | 462 |
| Thr | Asp | Ala | Gly | Ser | Glu | Val | Val | Gly | Trp | Tyr | Pro | Asp | Val | Thr | Ser |
| | -55 | | | | | -50 | | | | | -45 | | | | | |
| gac | agc | gtg | gtc | gtc | gag | gtg | gtc | gag | ggc | tcc | gac | gtc | gac | gtc | gac | 510 |
| Asp | Ser | Val | Val | Val | Glu | Val | Val | Glu | Gly | Ser | Asp | Val | Asp | Val | Asp |
| | -40 | | | | | -35 | | | | | -30 | | | | | |
| tcc | atc | gtc | gag | ggc | acg | ggc | gtc | gac | ccg | gcg | gtc | atc | gag | gtc | cag | 558 |
| Ser | Ile | Val | Glu | Gly | Thr | Gly | Val | Asp | Pro | Ala | Val | Ile | Glu | Val | Gln |
| -25 | | | | | -20 | | | | | -15 | | | | | -10 | |
| gag | gtc | tcc | gaa | cag | cct | cag | acc | tac | gcc | aac | atc | atc | ggc | ggc | ctg | 606 |

```
                Glu Val Ser Glu Gln Pro Gln Thr Tyr Ala Asn Ile Ile Gly Gly Leu
                    -5                  -1  1                   5 gcc tac tac atg agc tcg ggc cgc tgc tcg gtc ggc ttc ccc gcc           654
Ala Tyr Tyr Met Ser Ser Gly Arg Cys Ser Val Gly Phe Pro Ala
            10                  15                  20 acc aac agc tcc ggc cag ccg ggc ttc gtc acg gcg ggc cac tgc ggc       702
Thr Asn Ser Ser Gly Gln Pro Gly Phe Val Thr Ala Gly His Cys Gly
    25                  30                  35 acc gtc ggc acc ggc gtc acc atc ggc aac ggc cgc ggc acc ttc gag       750
Thr Val Gly Thr Gly Val Thr Ile Gly Asn Gly Arg Gly Thr Phe Glu
40                  45                  50                  55 cgc tcc gtg ttc ccc ggc aac gac gcc gcc ttc gtc cga ggc acg tcc       798
Arg Ser Val Phe Pro Gly Asn Asp Ala Ala Phe Val Arg Gly Thr Ser
                60                  65                  70 aac ttc acg ctg tac aac ctc gtc tac cgc tac agc ggc tac cag acc       846
Asn Phe Thr Leu Tyr Asn Leu Val Tyr Arg Tyr Ser Gly Tyr Gln Thr
                75                  80                  85 gtg acg ggc agc aac gcc gcc ccg atc ggc tcg tcc atc tgc cgt tcc       894
Val Thr Gly Ser Asn Ala Ala Pro Ile Gly Ser Ser Ile Cys Arg Ser
            90                  95                  100 ggt tcc acc acc ggc tgg cac tgc ggc acc atc cag gcc cgc aac cag       942
Gly Ser Thr Thr Gly Trp His Cys Gly Thr Ile Gln Ala Arg Asn Gln
    105                 110                 115 acc gtc cgg tac ccg cag ggc acc gtc tac tac ctg acc cgt acc aac       990
Thr Val Arg Tyr Pro Gln Gly Thr Val Tyr Tyr Leu Thr Arg Thr Asn
120                 125                 130                 135 gtg tgc gcc gag ccc ggc gac tcc gga ggc tcc ttc atc tcc gga acg      1038
Val Cys Ala Glu Pro Gly Asp Ser Gly Gly Ser Phe Ile Ser Gly Thr
                140                 145                 150 cag gcc cag ggc atg acc tcc ggc ggc tcc ggc aac tgc agc agc ggt      1086
Gln Ala Gln Gly Met Thr Ser Gly Gly Ser Gly Asn Cys Ser Ser Gly
                155                 160                 165 ggc acc acc ttc tac cag gag gtg gac ccg gtg gag agc gcc tgg ggc      1134
Gly Thr Thr Phe Tyr Gln Glu Val Asp Pro Val Glu Ser Ala Trp Gly
            170                 175                 180 gtg cga ctg cgc acc agc tag                                          1155
Val Arg Leu Arg Thr Ser
        185

<210> SEQ ID NO 12
<211> LENGTH: 384
<212> TYPE: PRT
<213> ORGANISM: Nocardiopsis lucentensis DSM 44048

<400> SEQUENCE: 12

Met  Arg Pro Ser Pro Val  Ile Ser Ala Leu Gly   Thr Gly Ala Leu
-195                -190                -185

Ala  Phe Gly Leu Val Ile  Thr Met Ala Pro Gly   Val Asn Ala Gly
-180                -175                -170

Thr  Val Pro Thr Pro Gln  Ala Pro Val Pro Asp   Asp Glu Ala Thr
-165                -160                -155

Thr  Met Leu Glu Ala Met  Glu Arg Asp Leu Asp   Leu Thr Pro Phe
-150                -145                -140

Glu  Ala Glu Glu Leu Phe  Glu Ala Gln Glu Glu   Ala Ile Asp Leu
-135                -130                -125

Asp  Glu Glu Ala Thr Glu  Ala Ala Gly Ala Ala   Tyr Gly Gly Ser
-120                -115                -110

Leu  Phe Asp Thr Glu Thr  His Glu Leu Val Leu   Val Thr Asp Val
-105                -100                -95                 -90
```

```
Asp Ala Val Glu Ala Val Glu Ala Thr Gly Ala Ala Glu Val Val
            -85              -80              -75

Ser His Gly Ser Asp Gly Leu Ala Asp Ile Val Glu Asp Leu Asn Ala
            -70              -65              -60

Thr Asp Ala Gly Ser Glu Val Val Gly Trp Tyr Pro Asp Val Thr Ser
        -55              -50              -45

Asp Ser Val Val Val Glu Val Val Glu Gly Ser Asp Val Asp Val Asp
        -40              -35              -30

Ser Ile Val Glu Gly Thr Gly Val Asp Pro Ala Val Ile Glu Val Gln
-25              -20              -15              -10

Glu Val Ser Glu Gln Pro Gln Thr Tyr Ala Asn Ile Ile Gly Gly Leu
            -5               -1  1                5

Ala Tyr Tyr Met Ser Ser Gly Gly Arg Cys Ser Val Gly Phe Pro Ala
            10               15               20

Thr Asn Ser Ser Gly Gln Pro Gly Phe Val Thr Ala Gly His Cys Gly
        25               30               35

Thr Val Gly Thr Gly Val Thr Ile Gly Asn Gly Arg Gly Thr Phe Glu
40               45               50               55

Arg Ser Val Phe Pro Gly Asn Asp Ala Ala Phe Val Arg Gly Thr Ser
            60               65               70

Asn Phe Thr Leu Tyr Asn Leu Val Tyr Arg Tyr Ser Gly Tyr Gln Thr
            75               80               85

Val Thr Gly Ser Asn Ala Ala Pro Ile Gly Ser Ser Ile Cys Arg Ser
            90               95              100

Gly Ser Thr Thr Gly Trp His Cys Gly Thr Ile Gln Ala Arg Asn Gln
        105              110              115

Thr Val Arg Tyr Pro Gln Gly Thr Val Tyr Tyr Leu Thr Arg Thr Asn
120              125              130              135

Val Cys Ala Glu Pro Gly Asp Ser Gly Gly Ser Phe Ile Ser Gly Thr
            140              145              150

Gln Ala Gln Gly Met Thr Ser Gly Gly Ser Gly Asn Cys Ser Ser Gly
            155              160              165

Gly Thr Thr Phe Tyr Gln Glu Val Asp Pro Val Glu Ser Ala Trp Gly
            170              175              180

Val Arg Leu Arg Thr Ser
            185

<210> SEQ ID NO 13
<211> LENGTH: 81
<212> TYPE: DNA
<213> ORGANISM: Bacillus clausii
<220> FEATURE:
<221> NAME/KEY: sig_peptide
<222> LOCATION: (1)..(81)

<400> SEQUENCE: 13
atgaagaaac cgttggggaa aattgtcgca agcaccgcac tactcatttc tgttgctttt      60
agttcatcga tcgcatcggc t                                                81

<210> SEQ ID NO 14
<211> LENGTH: 49
<212> TYPE: DNA
<213> ORGANISM: Artificial sequence
<220> FEATURE:
<223> OTHER INFORMATION: Primer
<220> FEATURE:
<221> NAME/KEY: misc_feature
```

<223> OTHER INFORMATION: Primer

<400> SEQUENCE: 14
gcttttagtt catcgatcgc atcggctgcg accgtaccgg ccgagccag                49

<210> SEQ ID NO 15
<211> LENGTH: 46
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: Primer

<400> SEQUENCE: 15
ggagcggatt gaacatgcga ttactaaccg gtcaccaggg acagcc                    46

<210> SEQ ID NO 16
<211> LENGTH: 40
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: Primer

<400> SEQUENCE: 16
gttcatcgat cgcatcggct gtcaccgcac ccaccgagcc                           40

<210> SEQ ID NO 17
<211> LENGTH: 45
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: Primer

<400> SEQUENCE: 17
ggagcggatt gaacatgcga ttagctggtg acgaggctga ggttc                     45

<210> SEQ ID NO 18
<211> LENGTH: 38
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: Primer

<400> SEQUENCE: 18
gttcatcgat cgcatcggct gtgaccgccc ccgccgag                             38

<210> SEQ ID NO 19
<211> LENGTH: 45
<212> TYPE: DNA
<213> ORGANISM: Artifical sequence
<220> FEATURE:
<221> NAME/KEY: misc_feature
<223> OTHER INFORMATION: Primer

<400> SEQUENCE: 19
ggagcggatt gaacatgcga ttagctcgtg acgaggctga ggttc                     45

<210> SEQ ID NO 20
<211> LENGTH: 41
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: Primer

<400> SEQUENCE: 20
gttcatcgat cgcatcggct gcgcccggcc ccgtccccca g           41

<210> SEQ ID NO 21
<211> LENGTH: 41
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: Primer

<400> SEQUENCE: 21
ggagcggatt gaacatgcga tcagctggtg cggatgcgaa c           41

<210> SEQ ID NO 22
<211> LENGTH: 37
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: Primer

<400> SEQUENCE: 22
gttcatcgat cgcatcggct gccccgccc cccagtc                 37

<210> SEQ ID NO 23
<211> LENGTH: 44
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: Primer

<400> SEQUENCE: 23
ggagcggatt gaacatgcga ttaggtgcgc agacgcaggc ccca        44

<210> SEQ ID NO 24
<211> LENGTH: 42
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: Primer

<400> SEQUENCE: 24
gttcatcgat cgcatcggct ggaaccgtac ccaccccccca gg         42

<210> SEQ ID NO 25
<211> LENGTH: 41
<212> TYPE: DNA

```
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: Primer

<400> SEQUENCE: 25
ggagcggatt gaacatgcga ttagctggtg cgcagtcgca c                     41

<210> SEQ ID NO 26
<211> LENGTH: 9
<212> TYPE: PRT
<213> ORGANISM: Nocardiopsis dassonvillei subsp. dassonvillei DSM 43235
<220> FEATURE:
<221> NAME/KEY: MISC_FEATURE
<223> OTHER INFORMATION: N-terminal

<400> SEQUENCE: 26

Ala Asp Ile Val Gly Gly Glu Ala Tyr
1               5

<210> SEQ ID NO 27
<211> LENGTH: 10
<212> TYPE: PRT
<213> ORGANISM: Nocardiopsis sp. DSM 16424
<220> FEATURE:
<221> NAME/KEY: MISC_FEATURE
<223> OTHER INFORMATION: N-terminal

<400> SEQUENCE: 27

Ala Asn Ile Ile Gly Gly Leu Ala Tyr Thr
1               5                   10
```